US009629664B2

(12) United States Patent
Altarac et al.

(10) Patent No.: US 9,629,664 B2
(45) Date of Patent: Apr. 25, 2017

(54) ANTERIOR CERVICAL PLATE

(71) Applicant: Neurostructures, Inc., Irvine, CA (US)

(72) Inventors: Moti Altarac, Irvine, CA (US); Joey Reglos, Lake Forest, CA (US)

(73) Assignee: Neurostructures, Inc., Irvine, CA (US)

( * ) Notice: Subject to any disclaimer, the term of this patent is extended or adjusted under 35 U.S.C. 154(b) by 518 days.

(21) Appl. No.: 14/159,024

(22) Filed: Jan. 20, 2014

(65) Prior Publication Data

US 2015/0201982 A1    Jul. 23, 2015

(51) Int. Cl.
*A61B 17/80* (2006.01)
*A61B 17/70* (2006.01)

(52) U.S. Cl.
CPC ...... *A61B 17/7059* (2013.01); *A61B 17/8042* (2013.01)

(58) Field of Classification Search
CPC ............ A61B 17/7059; A61B 17/8033; A61B 17/8042
USPC ... 606/246, 280, 70, 71, 286, 289, 290, 293, 606/294, 295, 296
See application file for complete search history.

(56) References Cited

U.S. PATENT DOCUMENTS

| 5,364,399 | A | 11/1994 | Lowery et al. |
| 5,549,612 | A | 8/1996 | Yapp et al. |
| 5,616,142 | A | 4/1997 | Yuan et al. |
| 5,616,144 | A | 4/1997 | Yapp et al. |
| 6,045,552 | A | 4/2000 | Zucherman et al. |
| 6,139,550 | A | 10/2000 | Michelson |
| 6,398,783 | B1 | 6/2002 | Michelson |
| 6,599,290 | B2 | 7/2003 | Bailey et al. |
| 6,602,255 | B1 | 8/2003 | Campbell et al. |
| 6,626,907 | B2 | 9/2003 | Campbell et al. |
| 6,652,525 | B1 | 11/2003 | Assaker et al. |
| 6,695,846 | B2 | 2/2004 | Richelsoph et al. |
| 6,964,664 | B2 | 11/2005 | Freid et al. |
| 7,175,623 | B2 | 2/2007 | Thramann et al. |
| 7,186,254 | B2 | 3/2007 | Dinh et al. |
| 7,220,263 | B2 | 5/2007 | Cordaro |
| 7,273,481 | B2 | 9/2007 | Lombardo et al. |

(Continued)

FOREIGN PATENT DOCUMENTS

| EP | 1520545 B1 | 11/2006 |
| EP | 1429675 B1 | 10/2007 |

(Continued)

*Primary Examiner* — Pedro Philogene
*Assistant Examiner* — David C Comstock
(74) *Attorney, Agent, or Firm* — Rimas Lukas

(57) ABSTRACT

An anterior cervical plate system is provided. The cervical plate includes an actuator and two locks located between two holes adapted to receive fasteners. Each lock includes a pair of fingers oppositely disposed from a fastener retaining flange. The retaining flange face the holes and the fingers face each other with the actuator located between the fingers. The actuator includes an elongated body. As the actuator is rotated from an unlocked to a locked position, the elongated body pushes both locks simultaneously outwardly to retain fasteners placed inside the holes. As the actuator is rotated in the opposite direction to an unlocked position, the elongated body catches hooks on the fingers to pull the locks inwardly away from holes. The locks are configured to prevent bone fasteners from backing out of the plate.

20 Claims, 26 Drawing Sheets

(56) References Cited

U.S. PATENT DOCUMENTS

| | | |
|---|---|---|
| 7,276,070 B2 | 10/2007 | Muckter |
| 7,278,997 B1 | 10/2007 | Mueller et al. |
| 7,288,094 B2 | 10/2007 | Lindemann et al. |
| 7,288,095 B2 | 10/2007 | Baynham et al. |
| 7,291,152 B2 | 11/2007 | Abdou |
| 7,306,605 B2 | 12/2007 | Ross |
| 7,318,825 B2 | 1/2008 | Butler et al. |
| 7,524,325 B2 | 4/2009 | Khalili |
| 7,601,170 B2 | 10/2009 | Winslow et al. |
| 7,651,517 B2 | 1/2010 | Konieczynski et al. |
| 7,662,154 B2 | 2/2010 | Ribeiro |
| 7,686,806 B2 | 3/2010 | Rhyne |
| 7,740,630 B2 | 6/2010 | Michelson |
| 7,803,157 B2 | 9/2010 | Michelson |
| 7,811,285 B2 | 10/2010 | Michelson |
| 7,815,666 B2 | 10/2010 | Baynham et al. |
| 7,824,432 B2 | 11/2010 | Michelson |
| 7,887,547 B2 | 2/2011 | Campbell et al. |
| 8,668,723 B2 | 3/2014 | Altarac et al. |
| 2002/0120270 A1 | 8/2002 | Trieu et al. |
| 2003/0093082 A1 | 5/2003 | Campbell et al. |
| 2003/0105462 A1 | 6/2003 | Haider |
| 2003/0105466 A1 | 6/2003 | Ralph et al. |
| 2003/0105467 A1 | 6/2003 | Ralph et al. |
| 2003/0125739 A1 | 7/2003 | Bagga et al. |
| 2003/0135216 A1 | 7/2003 | Sevrain |
| 2003/0153920 A1 | 8/2003 | Ralph et al. |
| 2003/0171753 A1 | 9/2003 | Collins et al. |
| 2003/0181912 A1 | 9/2003 | Michelson |
| 2003/0187440 A1 | 10/2003 | Richelsoph et al. |
| 2003/0187442 A1 | 10/2003 | Richelsoph et al. |
| 2003/0187509 A1 | 10/2003 | Lemole, Jr. |
| 2003/0191471 A1 | 10/2003 | Michelson |
| 2003/0191472 A1 | 10/2003 | Michelson |
| 2003/0208204 A1 | 11/2003 | Bailey et al. |
| 2003/0229348 A1 | 12/2003 | Sevrain |
| 2003/0236528 A1 | 12/2003 | Thramann |
| 2004/0006343 A1 | 1/2004 | Sevrain |
| 2004/0015169 A1 | 1/2004 | Gause |
| 2004/0019353 A1 | 1/2004 | Freid et al. |
| 2004/0024081 A1 | 2/2004 | Trieu et al. |
| 2004/0030336 A1 | 2/2004 | Khanna |
| 2004/0034352 A1 | 2/2004 | Needham et al. |
| 2004/0049279 A1 | 3/2004 | Sevrain |
| 2004/0068319 A1 | 4/2004 | Cordaro |
| 2004/0087945 A1 | 5/2004 | Ralph et al. |
| 2004/0087951 A1 | 5/2004 | Khalili |
| 2004/0092929 A1 | 5/2004 | Zindrick |
| 2004/0092947 A1 | 5/2004 | Foley |
| 2004/0097925 A1 | 5/2004 | Boehm, Jr. et al. |
| 2004/0097934 A1 | 5/2004 | Farris et al. |
| 2004/0097935 A1 | 5/2004 | Richelsoph et al. |
| 2004/0097938 A1 | 5/2004 | Alleyne |
| 2004/0097950 A1 | 5/2004 | Foley et al. |
| 2004/0106924 A1 | 6/2004 | Ralph et al. |
| 2004/0122426 A1 | 6/2004 | Michelson |
| 2004/0127897 A1 | 7/2004 | Freid et al. |
| 2004/0127899 A1 | 7/2004 | Konieczynski et al. |
| 2004/0127900 A1 | 7/2004 | Konieczynski et al. |
| 2004/0133205 A1 | 7/2004 | Thramann et al. |
| 2004/0153088 A1 | 8/2004 | Ralph et al. |
| 2004/0158246 A1 | 8/2004 | Assaker et al. |
| 2004/0177847 A1 | 9/2004 | Foley et al. |
| 2004/0181226 A1 | 9/2004 | Michelson |
| 2004/0181229 A1 | 9/2004 | Michelson |
| 2004/0186476 A1 | 9/2004 | Michelson |
| 2004/0204710 A1 | 10/2004 | Patel et al. |
| 2004/0204712 A1 | 10/2004 | Kolb et al. |
| 2004/0204713 A1 | 10/2004 | Abdou |
| 2004/0210314 A1 | 10/2004 | Michelson |
| 2004/0215192 A1 | 10/2004 | Justis et al. |
| 2004/0215195 A1 | 10/2004 | Shipp et al. |
| 2004/0220571 A1 | 11/2004 | Assaker et al. |
| 2004/0220572 A1 | 11/2004 | Michelson |
| 2004/0225290 A1 | 11/2004 | Ferree |
| 2004/0236333 A1 | 11/2004 | Lin |
| 2004/0236334 A1 | 11/2004 | Michelson |
| 2004/0236335 A1 | 11/2004 | Michelson |
| 2004/0243128 A1 | 12/2004 | Howland |
| 2004/0260306 A1 | 12/2004 | Fallin et al. |
| 2005/0015092 A1 | 1/2005 | Rathbun et al. |
| 2005/0015093 A1 | 1/2005 | Suh et al. |
| 2005/0027296 A1 | 2/2005 | Thramann et al. |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0038436 A1 | 2/2005 | Michelson |
| 2005/0043732 A1 | 2/2005 | Dalton |
| 2005/0059970 A1 | 3/2005 | Kolb |
| 2005/0059971 A1 | 3/2005 | Michelson |
| 2005/0075633 A1 | 4/2005 | Ross |
| 2005/0085816 A1 | 4/2005 | Michelson |
| 2005/0137597 A1 | 6/2005 | Butler et al. |
| 2005/0149021 A1 | 7/2005 | Tozzi |
| 2005/0149026 A1 | 7/2005 | Butler et al. |
| 2005/0149027 A1 | 7/2005 | Campbell et al. |
| 2005/0171551 A1 | 8/2005 | Sukovich et al. |
| 2005/0177160 A1 | 8/2005 | Baynham et al. |
| 2005/0177161 A1 | 8/2005 | Baynham et al. |
| 2005/0177163 A1 | 8/2005 | Abdou |
| 2005/0187552 A1 | 8/2005 | Michelson |
| 2005/0187553 A1 | 8/2005 | Grabowski et al. |
| 2005/0187554 A1 | 8/2005 | Michelson |
| 2005/0192576 A1 | 9/2005 | Michelson |
| 2005/0208095 A1 | 9/2005 | Hunter et al. |
| 2005/0209593 A1 | 9/2005 | Kolb |
| 2005/0216005 A1 | 9/2005 | Howland |
| 2005/0216009 A1 | 9/2005 | Michelson |
| 2005/0216010 A1 | 9/2005 | Michelson |
| 2005/0228386 A1 | 10/2005 | Ziolo et al. |
| 2005/0234455 A1 | 10/2005 | Binder et al. |
| 2005/0261690 A1 | 11/2005 | Binder et al. |
| 2005/0273105 A1 | 12/2005 | Konieczynski et al. |
| 2005/0277930 A1 | 12/2005 | Parsons |
| 2005/0277938 A1 | 12/2005 | Parsons |
| 2005/0283152 A1* | 12/2005 | Lindemann ........ A61B 17/7059 606/281 |
| 2006/0009845 A1 | 1/2006 | Chin |
| 2006/0030852 A1 | 2/2006 | Sevrain |
| 2006/0079961 A1 | 4/2006 | Michelson |
| 2006/0082015 A1 | 4/2006 | Happonen et al. |
| 2006/0085001 A1 | 4/2006 | Michelson |
| 2006/0149251 A1 | 7/2006 | Ziolo et al. |
| 2006/0149256 A1 | 7/2006 | Wagner et al. |
| 2006/0155298 A1 | 7/2006 | Mueller et al. |
| 2006/0161157 A1 | 7/2006 | Mosca et al. |
| 2006/0167456 A1 | 7/2006 | Johnston et al. |
| 2006/0189997 A1 | 8/2006 | Guenther et al. |
| 2006/0200134 A1 | 9/2006 | Freid et al. |
| 2006/0200147 A1 | 9/2006 | Ensign et al. |
| 2006/0229620 A1 | 10/2006 | Rothman et al. |
| 2006/0235405 A1 | 10/2006 | Hawkes |
| 2006/0241611 A1 | 10/2006 | Castro |
| 2006/0241616 A1 | 10/2006 | Konieczynski et al. |
| 2006/0276792 A1 | 12/2006 | Ensign et al. |
| 2006/0287653 A1 | 12/2006 | Rhyne |
| 2007/0083203 A1 | 4/2007 | Ribeiro |
| 2007/0123884 A1 | 5/2007 | Abdou |
| 2007/0185489 A1 | 8/2007 | Abdou |
| 2007/0203492 A1 | 8/2007 | Needham et al. |
| 2007/0213728 A1 | 9/2007 | Lindemann et al. |
| 2007/0213729 A1 | 9/2007 | Lindemann et al. |
| 2007/0213820 A1 | 9/2007 | Magerl et al. |
| 2007/0213828 A1 | 9/2007 | Trieu et al. |
| 2007/0225707 A1 | 9/2007 | Wisnewski et al. |
| 2007/0225717 A1 | 9/2007 | Hawkes |
| 2007/0225718 A1 | 9/2007 | Ensign |
| 2007/0233070 A1 | 10/2007 | Young |
| 2007/0233072 A1 | 10/2007 | Dickinson et al. |
| 2007/0233107 A1 | 10/2007 | Zielinski |
| 2007/0233108 A1 | 10/2007 | Stalcup et al. |
| 2007/0233110 A1 | 10/2007 | Muhanna et al. |
| 2007/0233117 A1 | 10/2007 | Butler et al. |
| 2007/0233118 A1 | 10/2007 | McLain |

(56) References Cited

U.S. PATENT DOCUMENTS

| | | |
|---|---|---|
| 2007/0233119 A1 | 10/2007 | Markworth |
| 2007/0233120 A1 | 10/2007 | Thramann et al. |
| 2007/0239158 A1 | 10/2007 | Trieu et al. |
| 2007/0270851 A1 | 11/2007 | Erickson et al. |
| 2007/0270965 A1 | 11/2007 | Ferguson |
| 2007/0276371 A1 | 11/2007 | Baynham et al. |
| 2007/0276405 A1 | 11/2007 | Huebner et al. |
| 2008/0021470 A1 | 1/2008 | Ross |
| 2008/0208260 A1 | 8/2008 | Truckai et al. |
| 2008/0208262 A1 | 8/2008 | Butler et al. |
| 2008/0208263 A1 | 8/2008 | Butler et al. |
| 2008/0208341 A1 | 8/2008 | McCormack et al. |
| 2008/0215097 A1 | 9/2008 | Ensign et al. |
| 2008/0228226 A1 | 9/2008 | Shamie |
| 2008/0228230 A1 | 9/2008 | Ferree |
| 2008/0234680 A1 | 9/2008 | Zaiser et al. |
| 2008/0234681 A1 | 9/2008 | Baynham |
| 2008/0234689 A1 | 9/2008 | Melkent et al. |
| 2008/0234748 A1 | 9/2008 | Wallenstein et al. |
| 2008/0234749 A1 | 9/2008 | Forstein |
| 2008/0234750 A1 | 9/2008 | Woods et al. |
| 2008/0234751 A1 | 9/2008 | McClintock |
| 2008/0234752 A1 | 9/2008 | Dahners |
| 2008/0234753 A1 | 9/2008 | Trieu |
| 2008/0234755 A1 | 9/2008 | Henderson et al. |
| 2008/0287999 A1 | 11/2008 | Markworth |
| 2008/0288001 A1 | 11/2008 | Cawley et al. |
| 2009/0131988 A1 | 5/2009 | Bush, Jr. et al. |
| 2009/0149888 A1 | 6/2009 | Abdelgany |
| 2009/0171397 A1 | 7/2009 | Rothman et al. |
| 2009/0177237 A1 | 7/2009 | Zucherman et al. |
| 2009/0177239 A1 | 7/2009 | Castro |
| 2009/0182341 A1 | 7/2009 | Link et al. |
| 2009/0182383 A1 | 7/2009 | Prybyla et al. |
| 2009/0187218 A1 | 7/2009 | Schaffhausen |
| 2009/0192549 A1 | 7/2009 | Sanders et al. |
| 2009/0210008 A1 | 8/2009 | Butler et al. |
| 2009/0222049 A1 | 9/2009 | Frigg et al. |
| 2009/0259226 A1 | 10/2009 | Michelson |
| 2009/0270926 A1 | 10/2009 | Hawkes |
| 2010/0042159 A1 | 2/2010 | Butler |
| 2010/0049256 A1 | 2/2010 | Jeon et al. |
| 2010/0069968 A1 | 3/2010 | Assaker et al. |
| 2010/0234897 A1 | 9/2010 | Fisher et al. |
| 2011/0054528 A1 | 3/2011 | Michelson |
| 2011/0106159 A1 | 5/2011 | Nazeck |
| 2011/0118784 A1 | 5/2011 | Baynham et al. |

FOREIGN PATENT DOCUMENTS

| | | |
|---|---|---|
| EP | 1841376 A2 | 10/2007 |
| EP | 1847229 A2 | 10/2007 |
| WO | WO2007037774 A1 | 4/2007 |
| WO | WO2007101266 A1 | 9/2007 |
| WO | WO2007103081 A2 | 9/2007 |
| WO | WO2007121080 A2 | 10/2007 |
| WO | WO2006138291 B1 | 11/2007 |
| WO | WO2007134199 A2 | 11/2007 |
| WO | WO2009089395 A2 | 7/2009 |
| WO | WO2009091770 A1 | 7/2009 |
| WO | WO2009091775 A2 | 7/2009 |

* cited by examiner

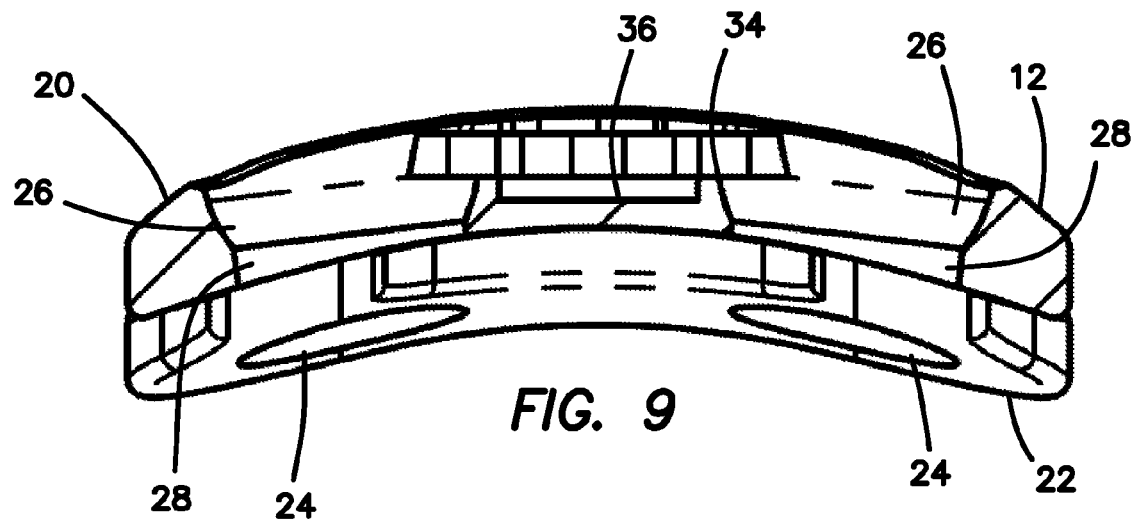
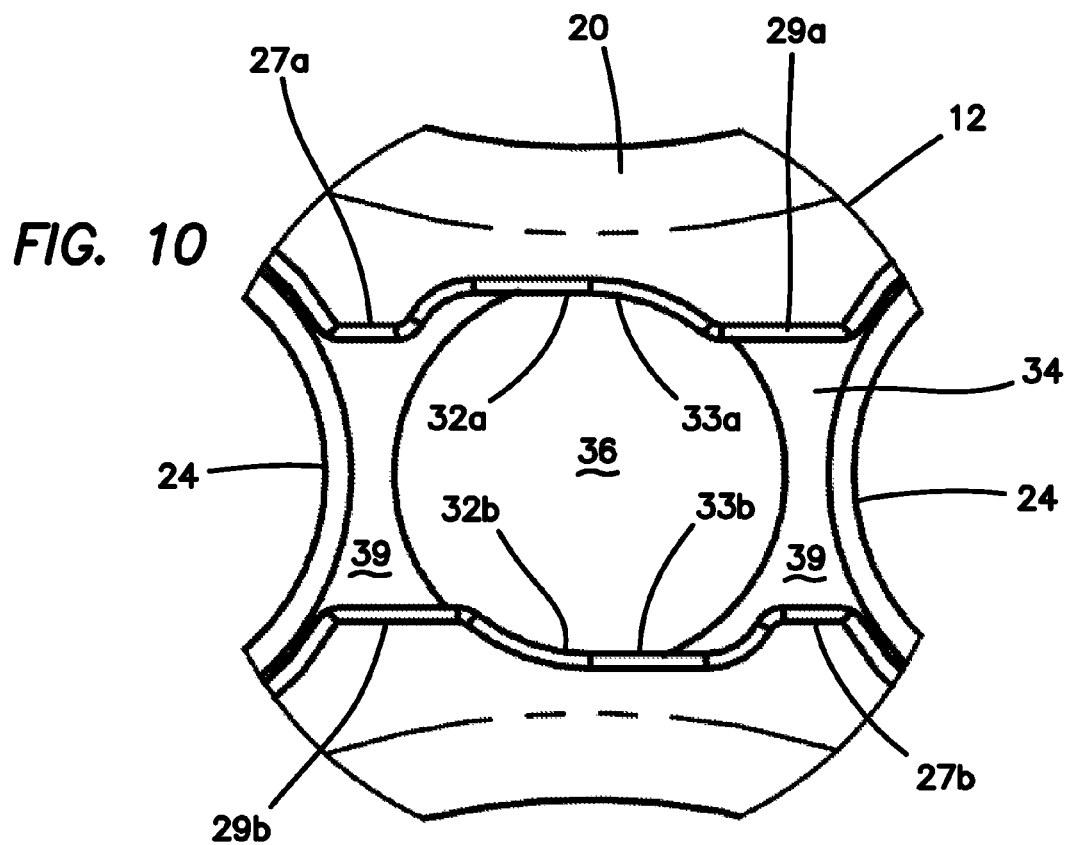

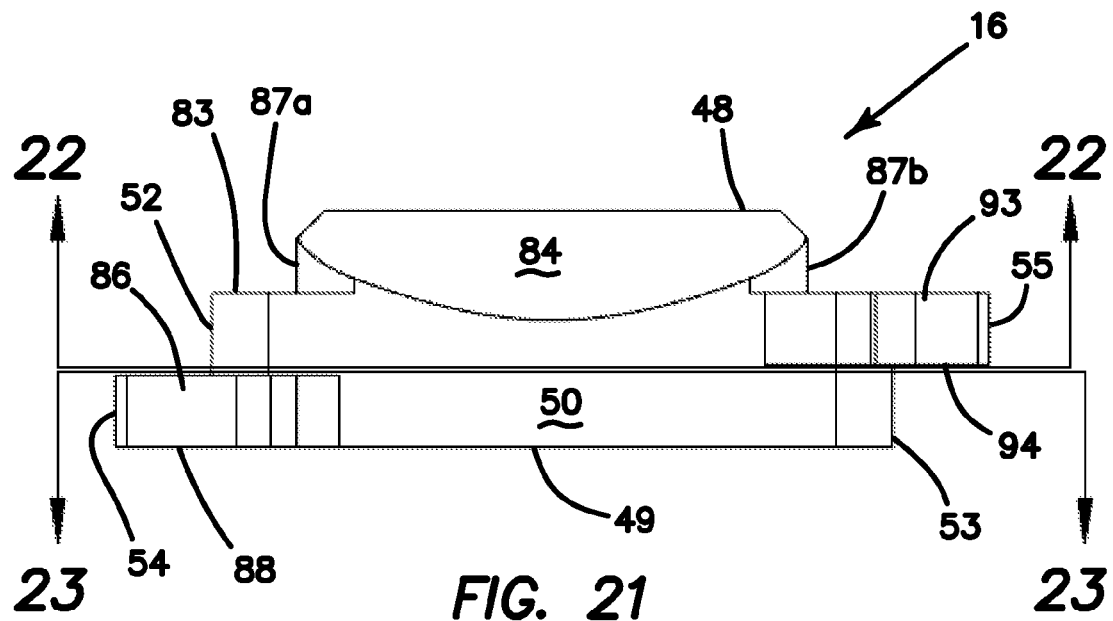
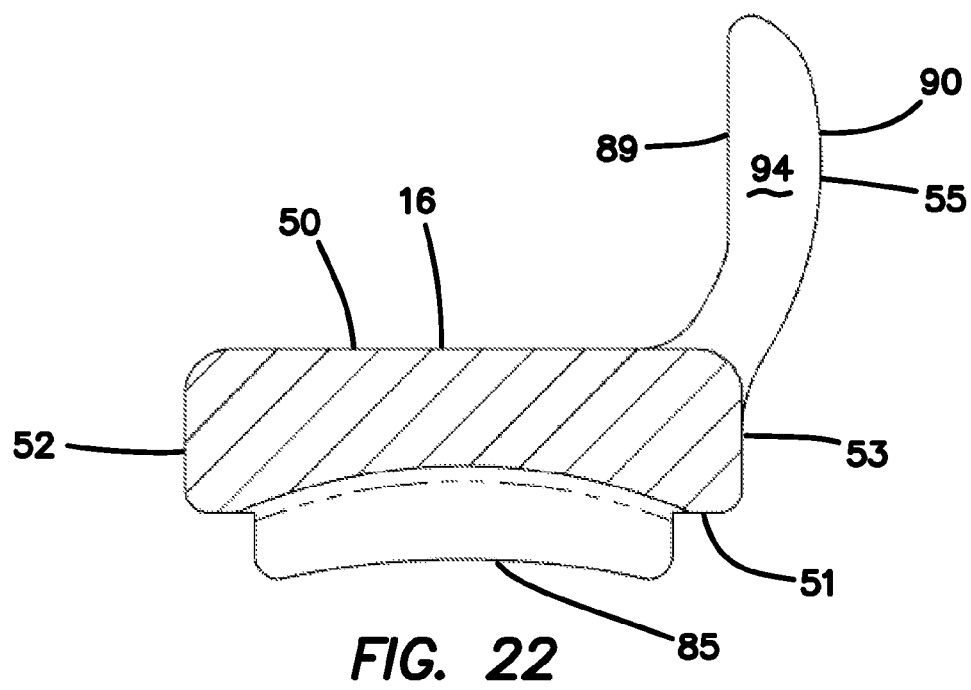

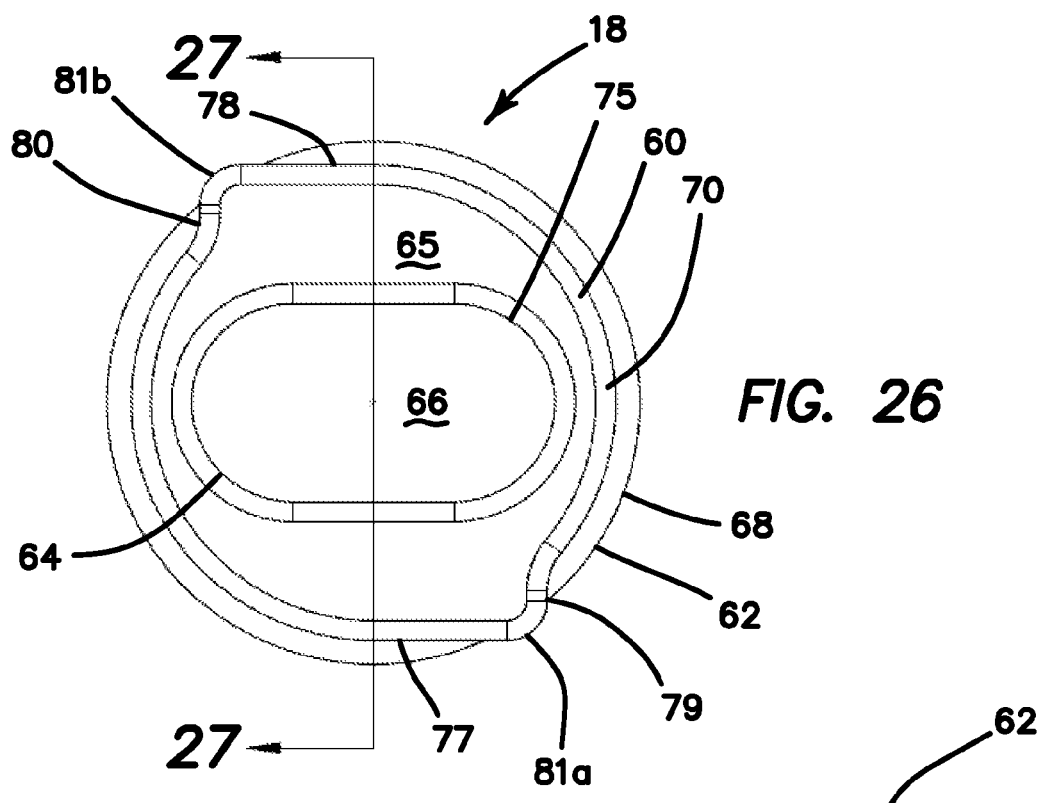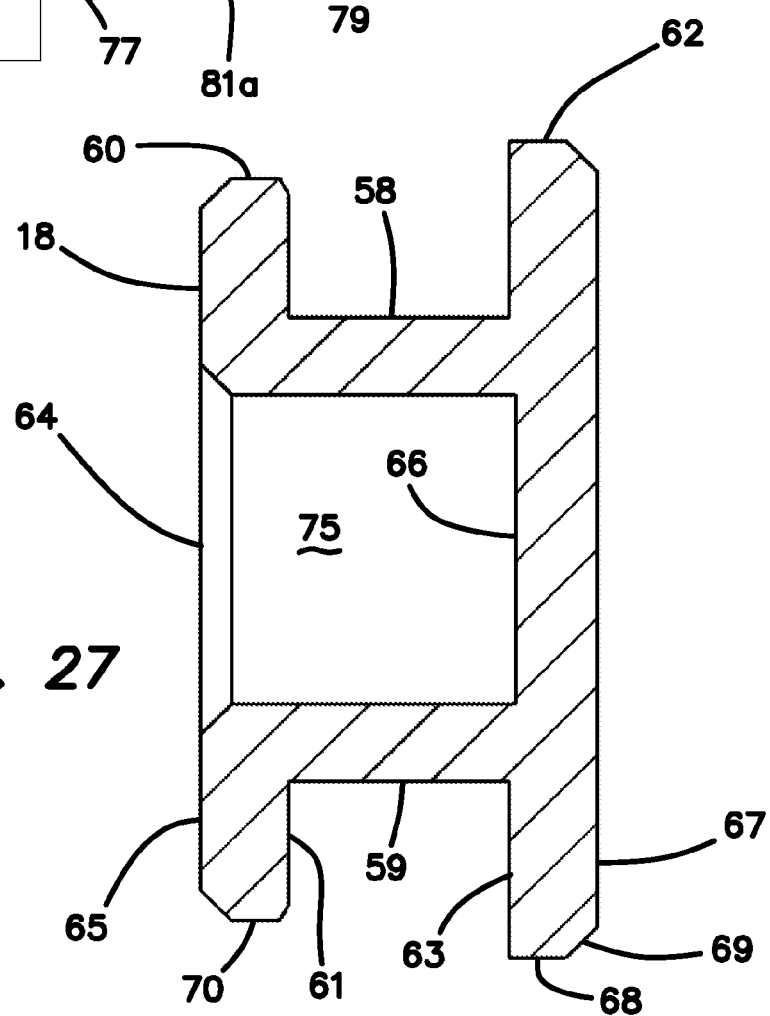

ANTERIOR CERVICAL PLATE

FIELD OF THE INVENTION

This invention relates to bone fixation plates and, more particularly, to fixation plates for the cervical spine that resist the backing out of associated bone fasteners.

BACKGROUND OF THE INVENTION

Anterior cervical plates are used for a variety of conditions to immobilize, stabilize or align cervical vertebrae. For example, after cervical spinal fusion surgery, cervical plates are used to add strength and rigidity to the adjoined vertebrae. Also, cervical plates secure vertebrae together where an intervening vertebra has been removed or replaced. In other cases, cervical plates are used to correct instability in the cervical spine caused by trauma, tumors, advanced degenerative discs, infection or congenital or acquired deformities.

A typical cervical plate includes an elongated rectangular plate that spans the distance between two or more vertebrae. The plate is curved to match the natural curvature of the spine at the location to which it is attached and bone screws are used to fasten the plate to the vertebral bodies. A pair of apertures is formed at one end of the plate for passing bone screws through and into a first vertebral body to secure the first end of the plate to the first vertebral body. A second pair of apertures is formed at the other end of the plate for passing bone screws through and into a second vertebral body to secure the second end of the plate to the second vertebral body. Thereby, the plate bridges two vertebral bodies. More vertebrae may be connected with a longer plate and a corresponding increased number of bone screw apertures and bone screws inserted therethrough at the intervening vertebral levels.

The cervical spine can be surgically approached anteriorly or posteriorly. In anterior cervical fusion surgery, an incision is made and the spine is approached from the front of the patient. The carotid sheath, muscles, trachea and esophagus are moved laterally to expose the cervical spine. Holes are drilled into the vertebral bodies or self-tapping screws are employed. The cervical plate is properly aligned on the vertebrae for the receipt of mounting screws and the plate is carefully and firmly attached. Sometimes fusion is accompanied by a discectomy in which a herniated disc is removed and a graft device is placed between the vertebral bodies to assist in fusion across levels. The plate may also include a window formed generally at a location between the two pairs of screw apertures through which bone growth progress may be observed. With the plate in position, the vertebrae are held by the plate in desired spatial relationships and orientations relative to each other, pressure is removed from the nerve roots and pain caused by the herniated disc or other condition is relieved.

Over time, the interface between the screws and the bone may present some problems of stability. Due to the anatomical structure of the cervical spine and the extreme anatomical forces that are brought to bear on the skeleton and transmitted to the cervical spine, the screws securing the plate to the spine may vibrate or toggle out of position. Also, the degeneration of vertebral bone quality may result in the screws loosening or becoming dislodged. As a result, bone screws securing the plate to the spine may move or back out of the vertebral body and plate. Due to the relative location to the esophagus and other connective tissue, if the bone screw securing the plate to the cervical spine backs out, the bone screw could impinge on the adjacent tissue and increase pain. Also, loosened screws may result instability of the joint and lead to increased pain for the patient.

Therefore, there is a need to provide a new and improved anterior cervical plate that resists fasteners, such as bone screws, from backing out of the plate and also from being loosened with respect to the plate before migrating out. Not only an improved and effective fastener retaining mechanism is required, but also, its design cannot add undue bulk to the plate. The anterior cervical plate must have a low profile due to the proximity of the implant site to the esophagus and other sensitive surrounding tissue. It is also preferable to keep the plate as narrow as possible to reduce the chances that the lateral edges rise off from the underlying vertebral body and cause pain where the curvature of the plate does not exactly match the patient's anatomy. Furthermore, there is a need for the anterior cervical plate to withstand anatomical forces and be easily implanted. Also, the screw retaining mechanism must be easily activated by the surgeon. This invention, as described in the detailed description, sets forth an improved anterior cervical plate with anti-back out protection that meets these needs.

SUMMARY OF THE INVENTION

According to one aspect of the invention, a bone plate system is provided. The bone plate system includes a plate having two adjacent through holes. Each through hole is configured to receive a bone fastener for attaching the plate to bone. The two through holes are substantially aligned along a lateral axis of the plate. The bone plate system includes an actuator located between the two through holes; the actuator is substantially aligned along the lateral axis of the plate with the two through holes. The actuator has a longitudinal axis and an outer surface. In cross-section of the actuator taken perpendicular to the longitudinal axis of the actuator, the outer surface defines a shape having a length greater than a width. The length is defined perpendicular to the longitudinal axis of the actuator and the width is defined perpendicular to the length and the longitudinal axis. In the cross-section, the outer surface comprises first and second opposing surface portions of the shape generally aligned with the length and third and fourth opposing surface portions of the shape generally aligned with the width. The actuator is connected to the plate such that the actuator rotates with respect to the plate. The bone plate system includes two locks movably coupled to the plate. Each lock has a pair of fingers on one side of the lock oppositely disposed from a fastener retaining flange on the other side of the lock. The fastener retaining flange of one lock is located between the actuator and one of the through holes and the fastener retaining flange of the other lock is located between the actuator and the other one of the through holes. The actuator is located between the fingers of both locks. The bone plate system includes two bone fasteners for placement into the two through holes. Each bone fastener has a head portion and is configured for insertion into a through hole such that at least a portion of the head portion is positioned distally of the fastener retaining flange. The bone plate includes an unlocked configuration in which the fastener retaining flanges are out of the pathway of the through holes to permit passage of the bone fasteners into or out of the through holes. The bone plate includes a locked configuration in which the fastener retaining flanges are in the pathway of the through holes and above at least a portion of the fasteners to prevent the bone fasteners from backing out of the through holes. The actuator is movable between a locked and unlocked configuration by rotation of the actuator relative to the plate which simultaneously moves both locks between the locked and unlocked configurations.

According to another aspect of the invention, a bone plate system is provided. The bone plate system includes a plate having two adjacent through holes. Each through hole is configured to receive a bone fastener for attaching the plate to bone. The two through holes are substantially aligned along a lateral axis of the plate. The bone plate system includes an actuator located between the two through holes. The actuator is substantially aligned along the lateral axis of the plate with the two through holes. The actuator is connected to the plate such that the actuator rotates with respect to the plate. The bone system plate further includes a first lock comprising a first finger and a second finger extending outwardly from an actuator-facing surface. The first lock also includes a fastener retaining flange extending outwardly from a fastener-facing surface. The first and second fingers are spaced apart and configured to receive the actuator between the first and second fingers. The bone plate system further includes a second lock comprising a third finger and a fourth finger extending outwardly from an actuator-facing surface. The second lock also includes a fastener retaining flange extending outwardly from a fastener-facing surface. The third and fourth fingers are spaced apart and configured to receive the actuator between the third and fourth fingers. The first finger is located beneath the fourth finger; the second finger is located above the third finger. The actuator is located between the first, second, third and fourth fingers. The bone plate system includes an unlocked configuration and a locked configuration configured such that, as the actuator is rotated from the unlocked configuration to a locked configuration, the actuator pushes both locks simultaneously outwardly away from the actuator and as the actuator is rotated from the locked configuration to the unlocked configuration the actuator simultaneously moves both locks inwardly toward the actuator.

According to another aspect of the invention, a bone plate system is provided. The bone plate system includes a plate having two adjacent through holes adapted to receive fasteners. The bone plate system includes an actuator comprising an elongated body. The bone plate system further includes two locks. Each lock includes a pair of fingers oppositely disposed from a fastener retaining flange. One of the pair of fingers includes a hook at the distal end of the finger. The actuator and two locks are connected to the plate such that the actuator and two locks are movable with respect to the plate. The actuator and two locks are located between the two through holes such that the retaining flanges face the through holes and the fingers face each other. The actuator is located between the fingers. The bone plate system includes a locked position and unlocked position. As the actuator is rotated from an unlocked to a locked position, the elongated body pushes both locks simultaneously outwardly to retain fasteners placed inside the through holes and as the actuator is rotated in an opposite direction to an unlocked position, the elongated body catches the hooks on the locks to simultaneously pull the locks inwardly away from the through holes.

BRIEF DESCRIPTION OF THE DRAWINGS

FIG. 9 is a cross-sectional view taken along line 9-9 of FIG. 8 of a plate according to the present invention.

FIG. 10 is a sectional view of section 10 of FIG. 8 of a plate according to the present invention.

FIG. 21 is an end elevational view of a lock according to the present invention.

FIG. 22 is a cross-sectional view taken along line 22-22 of FIG. 21 of a lock according to the present invention.

FIG. 26 is a top planar view of an actuator according to the present invention.

FIG. 27 is a cross-sectional view taken along line 27-27 of FIG. 26 of an actuator according to the present invention.

DETAILED DESCRIPTION OF THE INVENTION

Figure 1:
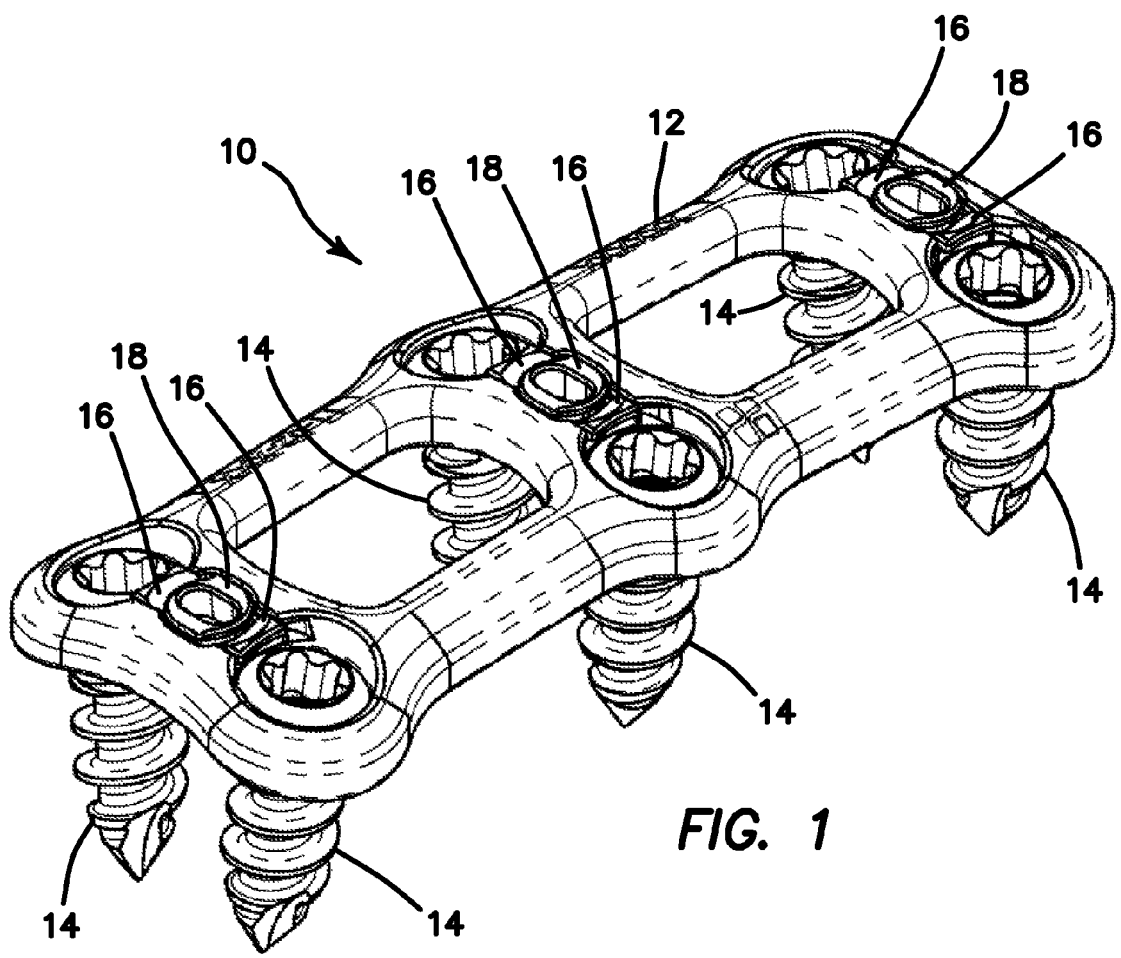
FIG. 1 is a top perspective view of an anterior cervical plate system according to the present invention.
Figure 2:
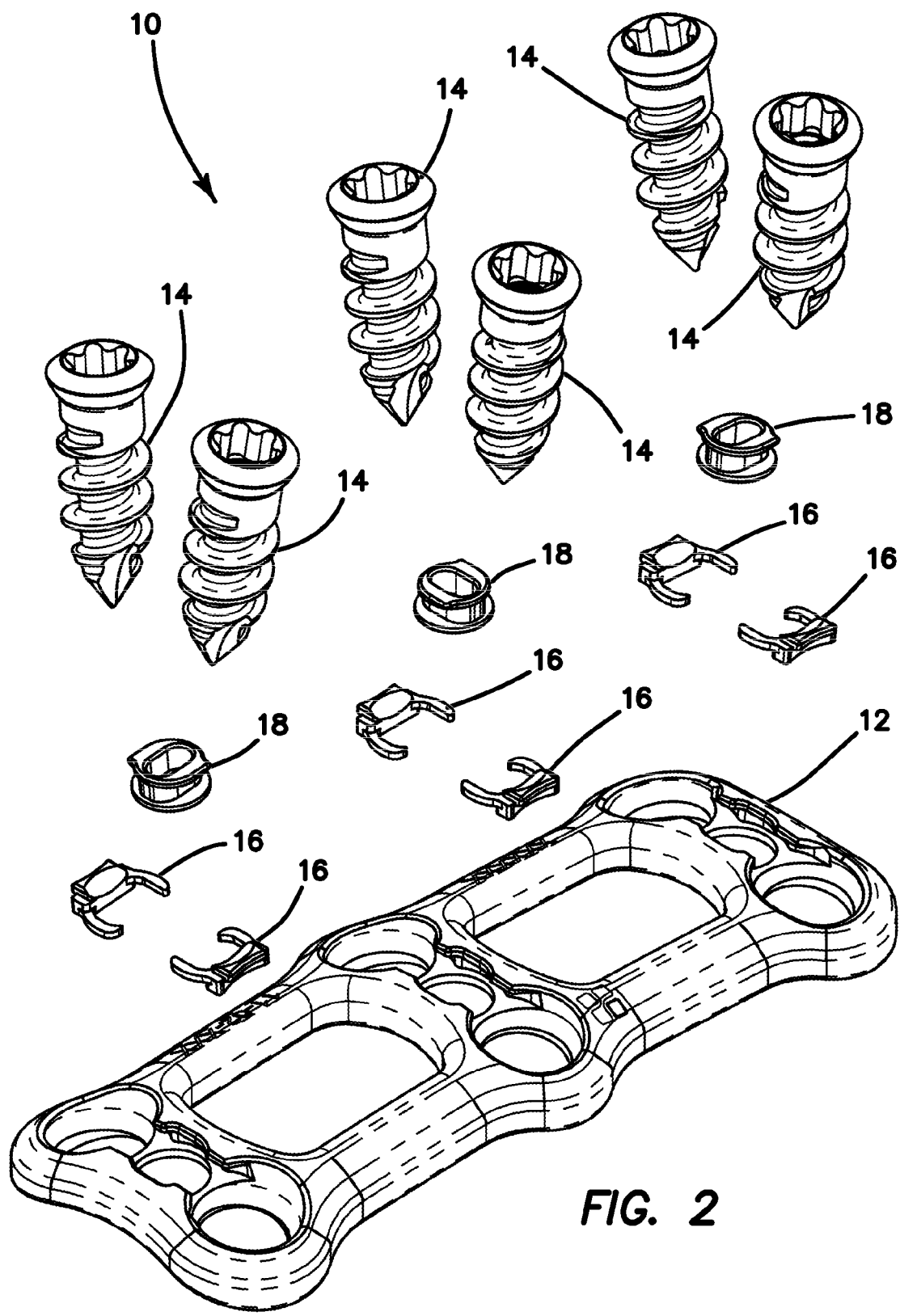
FIG. 2 is a top perspective exploded view of an anterior cervical plate system according to the present invention.
Figure 3:
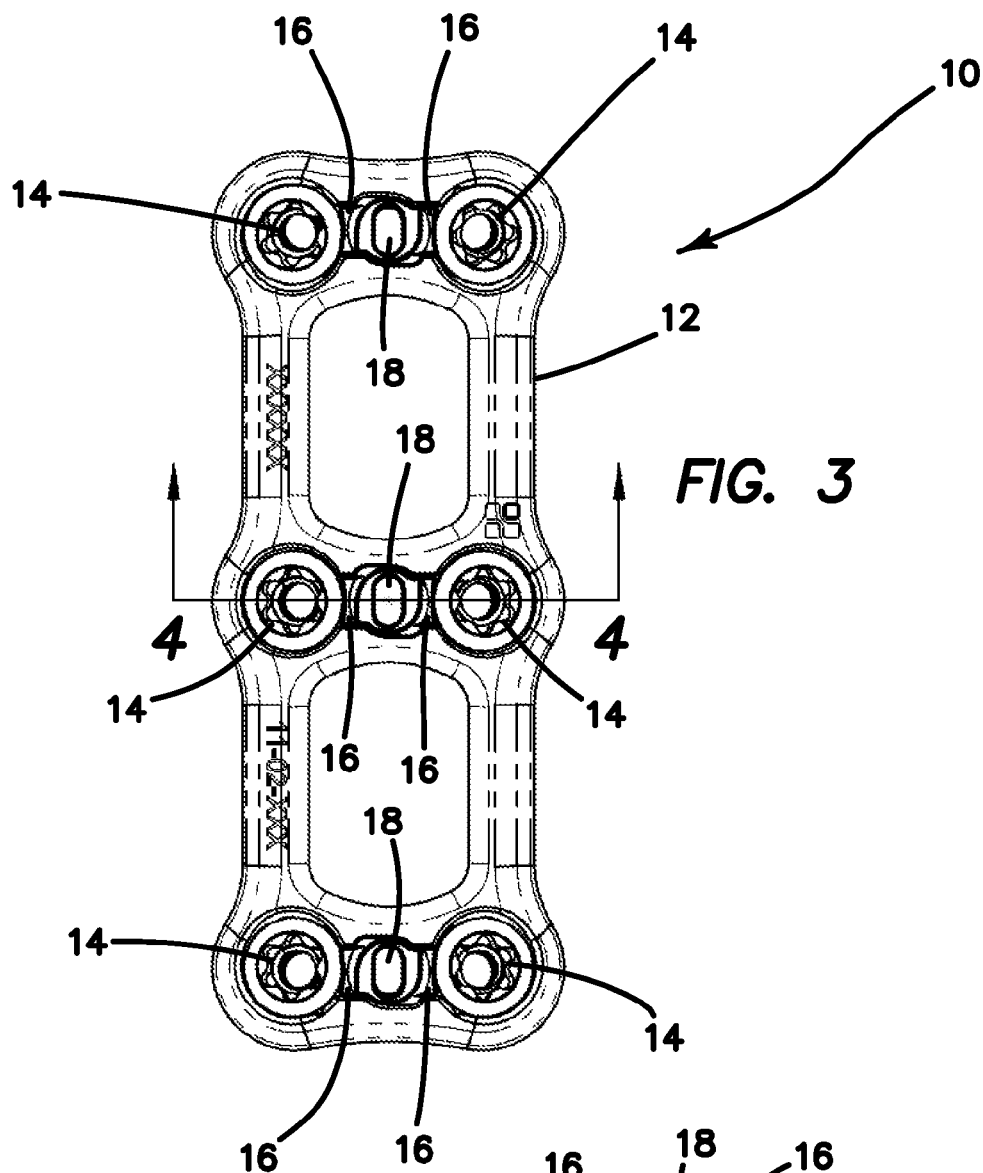
FIG. 3 is a top planar view of an anterior cervical plate system in an unlocked configuration according to the present invention.

FIGS. 1-6 depict a cervical plate system 10 according to one variation of the invention that may be used to stabilize or fuse vertebral bodies in the cervical or other region of the spine. The anterior cervical plate system 10 that is shown in FIGS. 1-6 is a two-level bone fixation plate that is configured to span across and fixate three vertebrae of the cervical spine although the cervical plate system 10 may be a single level or any multilevel anterior cervical plate spanning two or more vertebral bodies. The anterior cervical plate system 10 comprises a plate 12 having fasteners 14 retained by locks 16 activated by actuators 18. The cervical plate system 10 includes an unlocked position depicted in FIGS. 3-4 in which the locks 16 do not cover the fasteners 14 and locked position depicted in FIGS. 5-6 in which the actuators 18 are rotated to move the locks 16 into a fixed position covering the fasteners 14.

Figure 11:
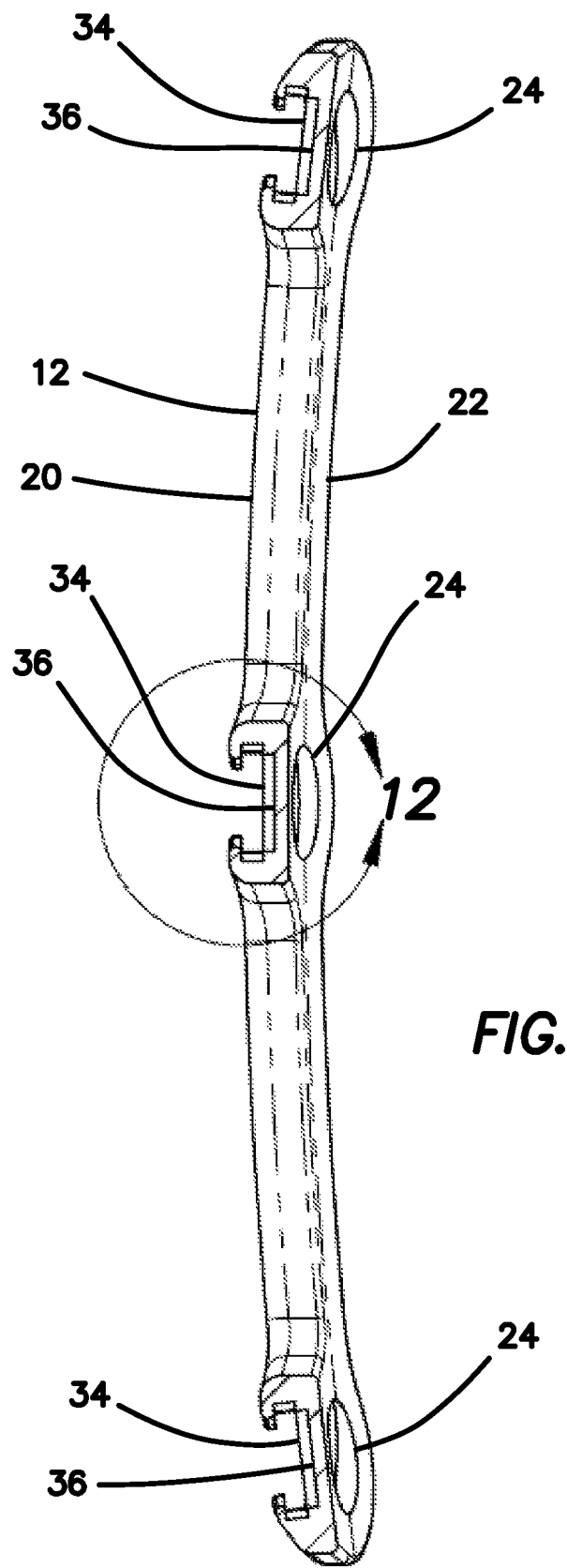
FIG. 11 is a cross-sectional view taken along line 11-11 of FIG. 8 of a plate according to the present invention.

Turning now to FIGS. 7-13, the plate 12 will now be described in greater detail. The plate 12 includes an upper surface 20 or anterior surface that faces the patient's soft tissue and esophagus when installed and a lower surface 22 or posterior surface facing the vertebral bodies to be immobilized. The upper surface 20 and lower surface 22 are interconnected by curved side walls and end walls to form a generally rectangular shape that is symmetrical about a midline. As best seen in FIGS. 9 and 11, the gently curved structure of the rectangular plate 12 complements the natural curved structure of the vertebral bodies and lordotic curvature of the cervical spine. The corners of the plate are rounded to reduce or eliminate irritation of the esophagus and the surrounding tissue. The plate 12 is sized and shaped for use on an anterior aspect of the cervical spine although one skilled in the art may use the device in other regions of the spine and other skeletal fixations. The plate 12, which resides atop the vertebral bodies, has a low profile so as to minimally impinge on adjacent tissues.

The plate 12 and other components of the cervical plate system 10 are made from suitable biocompatible material such as stainless steel, titanium and or any other metal or metal alloy. One or more components may be made of non-metal materials including but not limited to polymer, carbon reinforced polyetheretherketone (PEEK) or one or more biocompatible ceramics. The plate 12 may be additionally configured to promote bone ingrowth to the plate such as a portion of the plate being made of porous material or being roughened by mechanical blasting or plasma spraying with metal particles of one or more sizes. The plate 12 may also be coated with bio-active material, therapeutic agents for enhancing bone fusion and ingrowth, bone morphogenic proteins, growth factors and the like.

Still referencing FIGS. 7-13, the plate 12 includes a plurality of through holes 24 extending through the cervical plate 12 from the upper surface 20 and through the lower surface 22. The holes 24 are configured to receive bone fasteners 14 passed there through. As best seen in FIG. 9, each hole 24 includes a head-receiving portion 26 near the upper surface 20 connected to a smaller shank-receiving portion 28 near the lower surface 22 to, thereby, in one variation, provide a seat for the head portion of the fastener 14 at a ledge formed at the intersection of the head-receiving portion 26 and shank-receiving portion 28. The head-receiving portion 26 is recessed from the top surface 20 such that the head of the fastener 14 does not protrude beyond the upper surface 20 of the plate 12 in order to maintain a low profile for the plate 12. Each through hole 24 may have a scalloped or larger exit opening at the lower surface 22 to allow room for the angulation of inserted fasteners 14. The head-receiving portion 26 is shaped to complement the shape of the head of the fastener 14. For example, the head-receiving portion 26 forms a frustoconical or curved surface configured for a complimentary frustoconical or curved outer surface of the fastener 14. In one variation, the size of the through hole 24 is configured such that the head-receiving portion 26 and shank-receiving portion 28 are both large enough to allow a bone fastener 14 to pass all the way through the plate 12 without any hindrance and a retention ring is employed in the through hole 24 to reduce the size of the through hole 24 such that the head portion of the fastener 14 is not allowed to pass through the retention ring. In another variation, the shank-receiving portion 28 of the through hole 24 is smaller than the head-receiving portion 26 without the presence of a retention ring such that the head portion of a fastener 14 is not allowed to pass into the shank-receiving portion 28 of the through hole 24 and wherein the presence of the retention ring, if one is employed, further reduces the opening at the head-receiving portion 26 of the through hole 24. An undercut (not shown) in the through hole 24 such as in the location of the head-receiving portion 26 may be formed and configured to mate with the fastener 14 or retention ring if one is used to, thereby, couple the retention ring to the through hole 24 as the retention ring is compressed and then inserted into or under the undercut. In another variation, the through hole 24 is slightly elliptical in shape that matches a slightly elliptical retention ring which can be inserted in the conforming direction and then rotated into a non-conforming orientation to be retained within the through hole 24 by compression fit engagement therewith.

Figure 4:
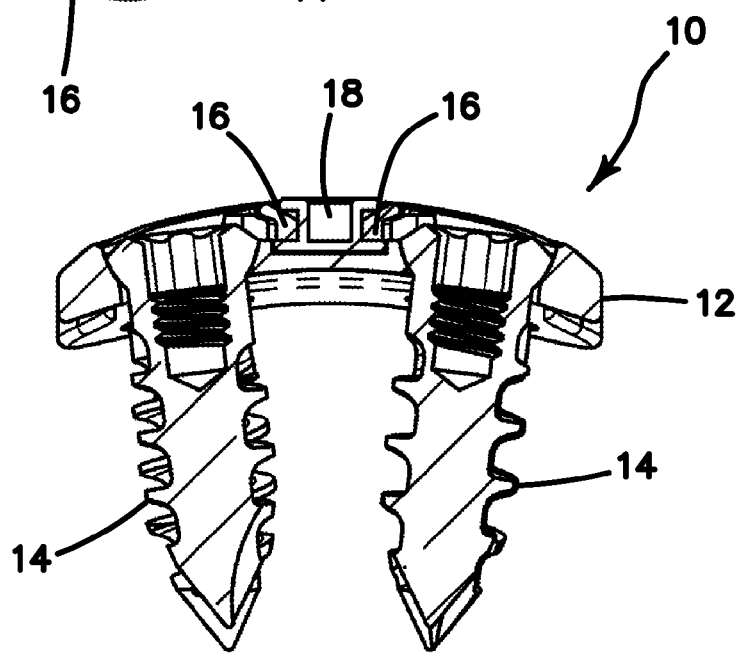
FIG. 4 is a cross-sectional view taken along line 4-4 of FIG. 3 of an anterior cervical plate system according to the present invention.
Figure 5:
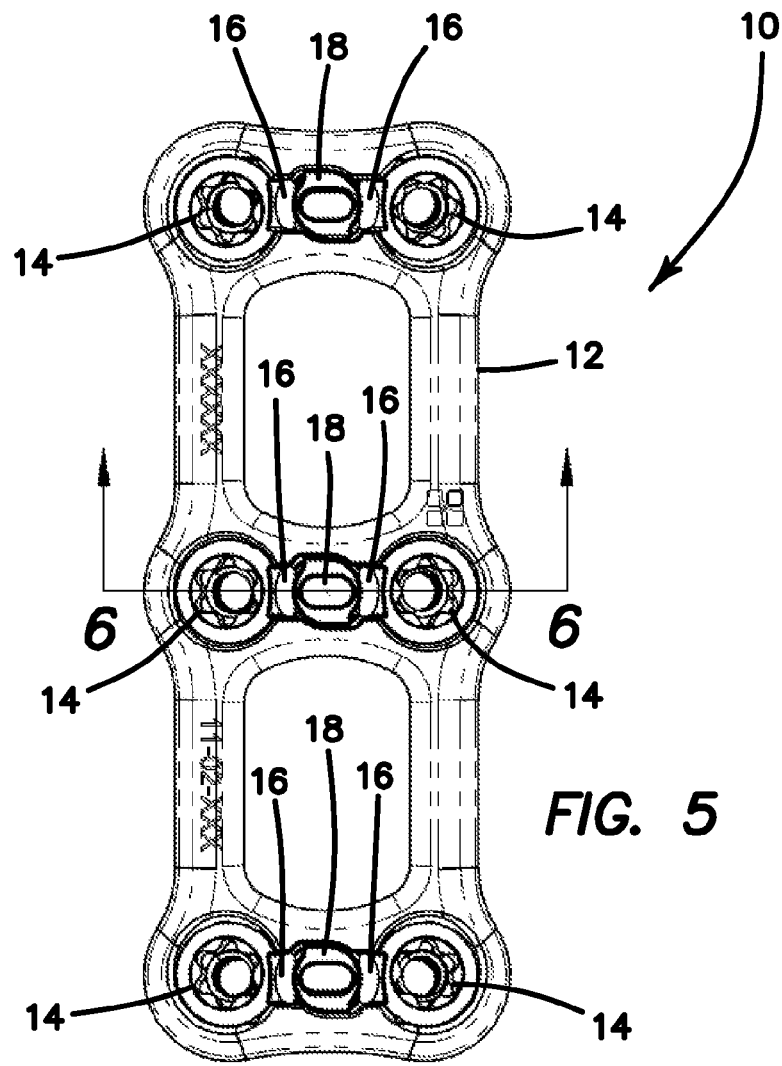
FIG. 5 is a top planar view of anterior cervical plate system in a locked configuration according to the present invention.
Figure 6:
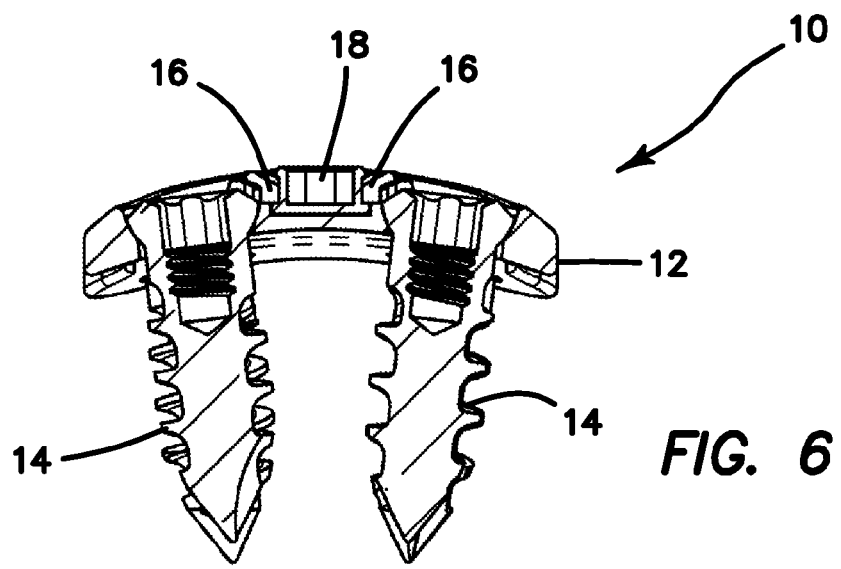
FIG. 6 is a cross-sectional view taken along line 6-6 of FIG. 5 of an anterior cervical plate system according to the present invention.
Figure 7:
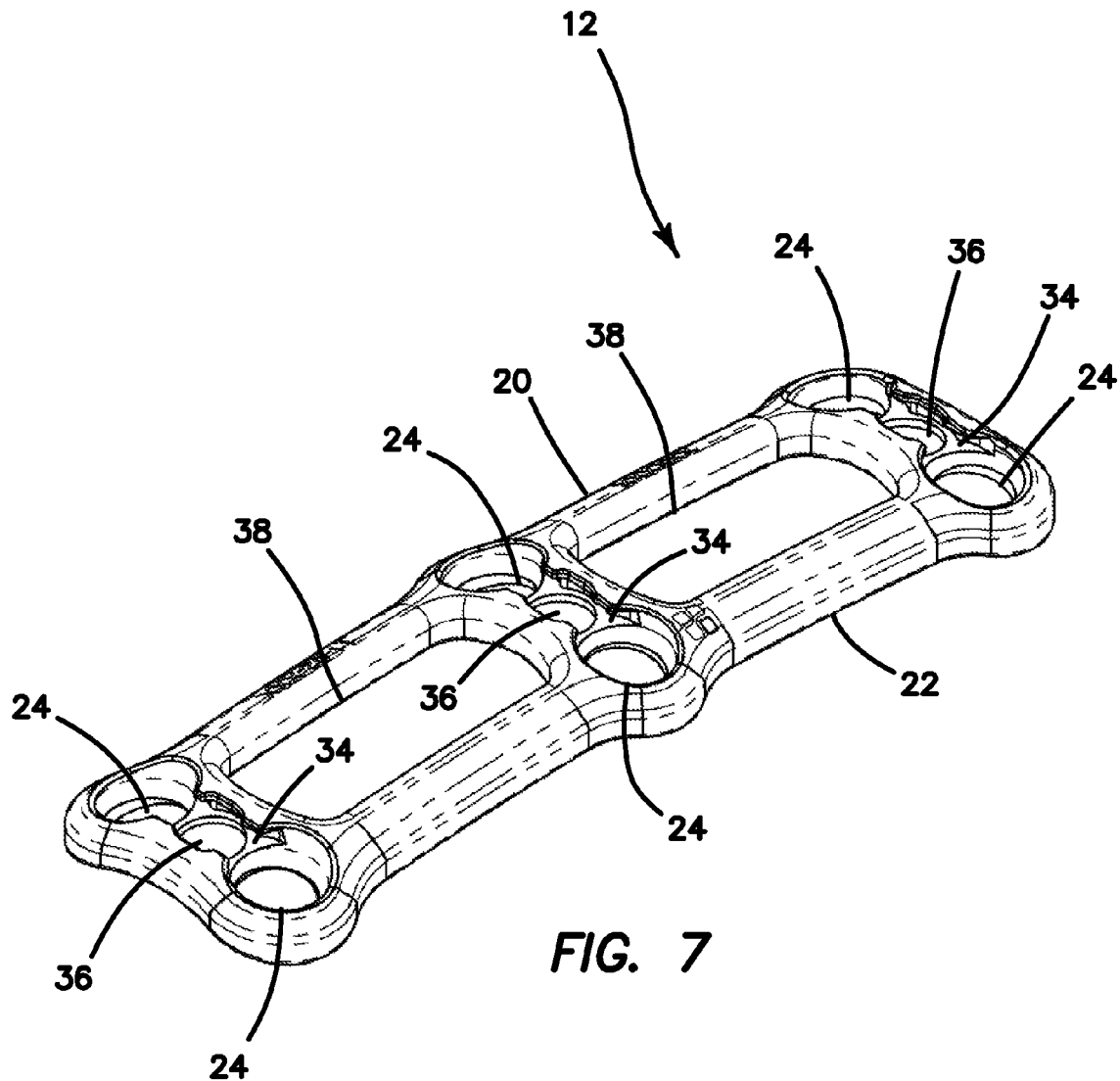
FIG. 7 is a top perspective view of a plate according to the present invention.
Figure 8:
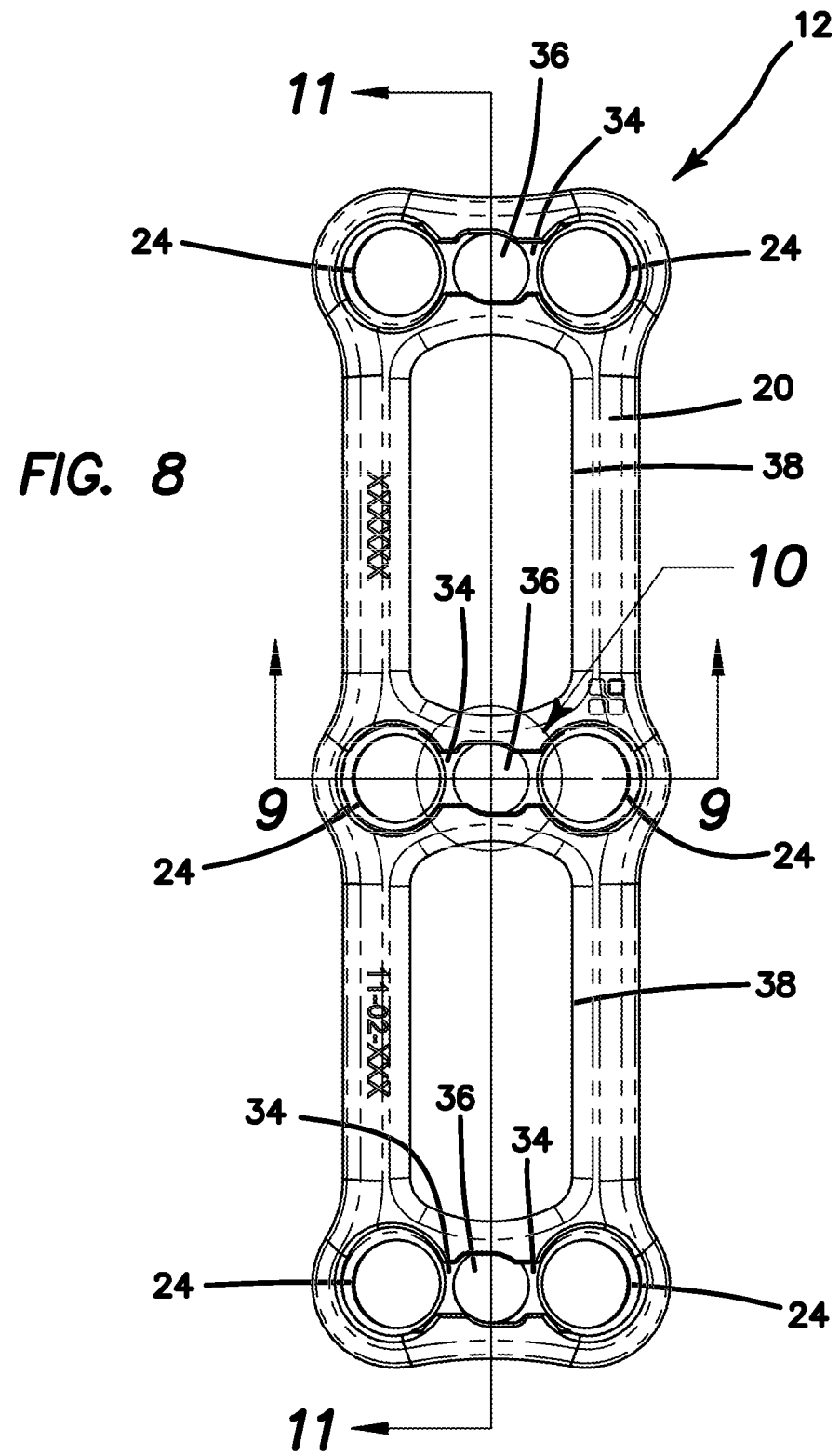
FIG. 8 is a top planar view of a plate according to the present invention.

FIGS. 7-13 depict a plate 12 having three sets or three pairs of fastener through holes 24 spaced-apart along the plate centerline for driving fasteners 14 into and stabilizing three vertebral bodies for creating a two-level construct. Each set of fastener through holes 24 includes two holes 24 spaced apart from each other along the centerline of the anterior cervical plate 12. Each set or pair of through holes 24 is adapted for receiving two fasteners 14 to be driven into a single vertebral body. The longitudinal axes of a pair of through holes 24 diverge relative to each other such that a pair of fasteners 14 placed therein diverge slightly relative to each other at a desired angled as best seen in FIGS. 4 and 6.

Figure 12:
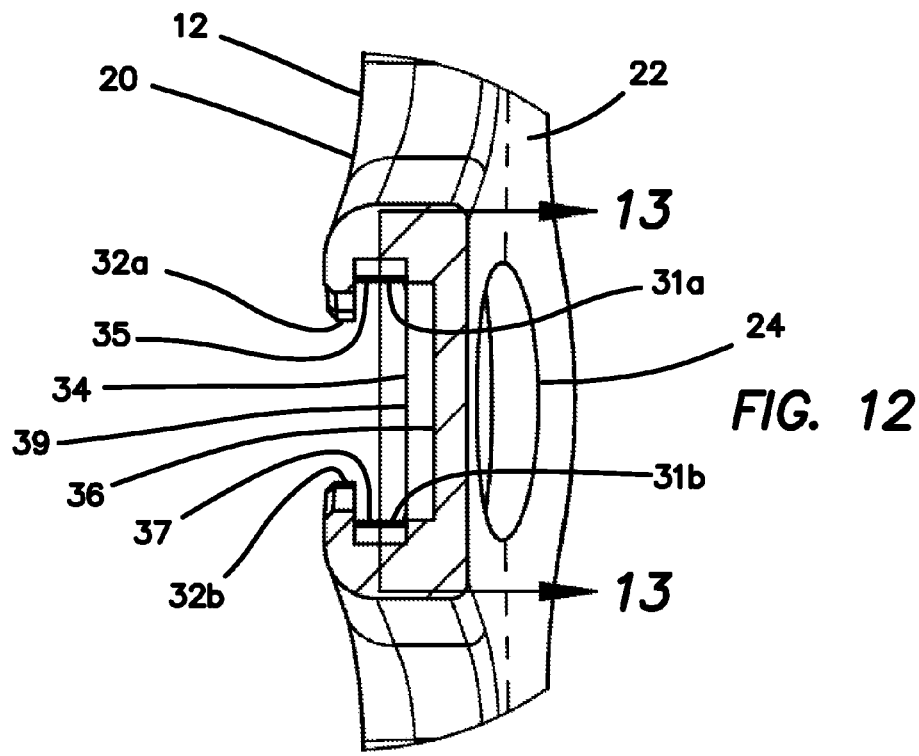
FIG. 12 is a sectional view of section 12 of FIG. 11 of a plate according to the present invention.
Figure 13:
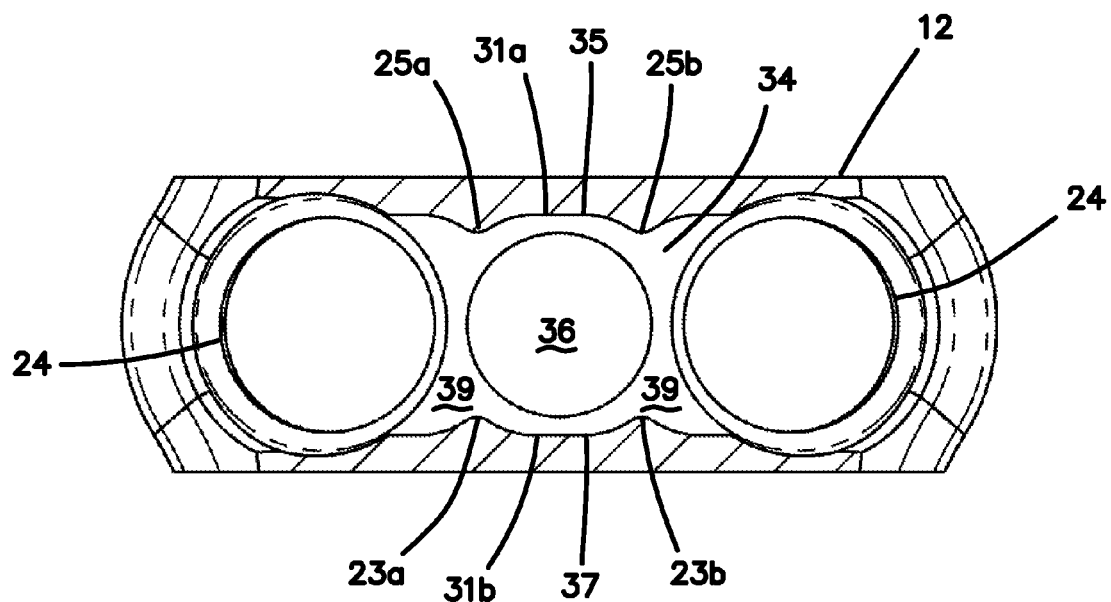
FIG. 13 is a cross-sectional view taken along line 13-13 of FIG. 12 of a plate according to the present invention.

The plate 12 further includes a recess 34 located between the through holes 24 of each pair of through holes 24. The recess 34 extends between the two adjacent through holes 24 and is in communication or interconnected with them. The recess 34 is configured for receiving the locks 16 and actuator 18 such that the locks 16 and actuator 18 do not protrude from the upper surface 20 of the plate 12 in order to maintain the desired low profile and such that the locks 16 and the actuator 18 remain connected to the plate 12. The recess 34 includes a base surface 39 best seen in FIGS. 10 and 13. The recess 34 extends along a z-axis from the base surface 39 to the upper surface 20 of the plate 12. A circular actuator well 36 is formed in the recess 34 at the centerline and is configured to receive and/or couple the actuator 18 to the plate 12. In one variation, the actuator 18 and well 36 are configured to snap-fit together or be connected together by any other means known in the art. The well 36 extends downwardly from the base surface 39 towards the lower surface 22 of the plate 12. The recess 34 includes a first sidewall 35 oppositely disposed from a second sidewall 37 as best seen in FIGS. 12-13. The sidewalls 35, 37 extend from the base surface 39 of the recess 34 upwardly and interconnect to the upper surface 20. Each of the sidewalls 35, 37 includes a receiving portion 31a, 31b and an overhang portion 32a, 32b, respectively, as depicted in FIG. 12. The receiving portion 31a, 31b is located between the base surface 39 and the overhang portion 32a, 32b. The overhang portion 32a, 32b transitions into the upper surface 20. The plate 12 also includes two larger openings 38 located between each pair of through holes 24 that effectively reduce the overall weight of the plate 12 and provide a visualization pathway to monitor bone graft progress between the vertebral bodies.

With reference to FIG. 10, the overhang portion 32a, 32b transitions into the upper surface 24 such that the through holes 24 for the fasteners 14 are not covered. Each overhang portion 32a, 32b in the location of the recess 34 includes an indentation or curved portion 33a, 33b interconnected between a stop 29a, 29b and a transition surface 27a, 27b. The indentation or curved portions 33a, 33b near the stop 29a, 29b partially covers the well 36. The indentation or curved portion 33a, 33b may be curved throughout or may include straight surfaces as shown in FIG. 10. The stop 29a, 29b is substantially a straight surface; however, the invention is not so limited. The stop 29a, 29b is configured to provide an abutment against at least a portion of the actuator 18, in particular, the stop 29a, 29b serves as an abutment for the upper body of the actuator 18 as will be described in greater detail below. The overhang portion 32a, 32b is configured to not only retain the actuator 18 and locks 16 but also permit the actuator 18 to rotate relative to the plate 12 between a locked and unlocked orientation. In one variation, the actuator 18 is configured to rotate approximately 90 degrees relative to the plate 12 with the unlocked configuration at approximately zero degrees and the locked configuration at approximately 90 degrees. The stops 29a, 29b serve the limit the rotation of the actuator 18 relative to the plate 12. The actuator 18 rotates clockwise into the locked position and counterclockwise into the unlocked position. Of course, the invention is not limited to the degree to which the actuator 18 rotates relative to the plate 12. As can be seen in FIG. 10, stop 29a is directly opposite from the transition surface 27b along the lateral axis and stop 29b is directly opposite from transition surface 27a. Stop 29a is diagonally opposite from stop 29b using the well 36 as a reference.

Turning now to FIG. 13, the receiving portion 31a, 31b of the sidewalls 35, 37 will now be described. The receiving portion 31a, 31b is configured to receive the locks 16. In particular, the locks 16 are located in the receiving portion 31a, 31b along the sidewalls 35, 37, respectively, between the overhang portion 32a, 32b and the base surface 29. In the receiving portion or intermediate portion 31a, the first sidewall 35 includes two protrusions 25a, 25b that extend inwardly toward the recess 34. In the receiving portion or intermediate portion 31b, the second sidewall 37 includes two protrusions 23a, 23b that extend inwardly toward the recess 34. The protrusions 25a, 25b are oppositely located from protrusions 23a, 23b, respectively. The protrusions 23a, 23b, 25a, 25b are configured to retain the locks 16. In particular, the protrusions 23a, 23b, 25a, 25b are configured to retain the locks 16 from unlimited translation along the lateral axis of the plate. The protrusions 23a, 23b, 25a, 25b also retain the actuator 18 in the locked and unlocked positions. In particular, when the actuator 18 is turned clockwise from the unlocked position to the locked position, the actuator 18 is turned past protrusions 23a and 25b which also assist in keeping the actuator 18 in the locked position. Also, when the actuator 18 is turned counterclockwise from the locked position to the unlocked position, the actuator is turned past protrusions 23a and 25b which also help to keep the actuator 18 in the unlocked position. Of course, the system may be configured such that clockwise rotation effects an unlocked orientation.

Figure 14:
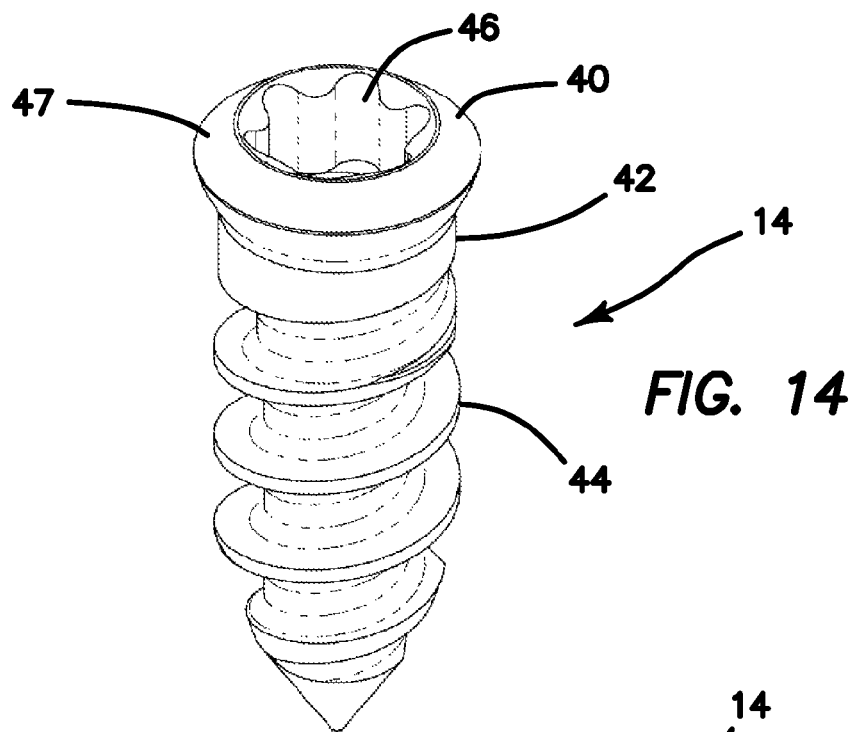
FIG. 14 is a top perspective view of a fastener according to the present invention.
Figure 15:
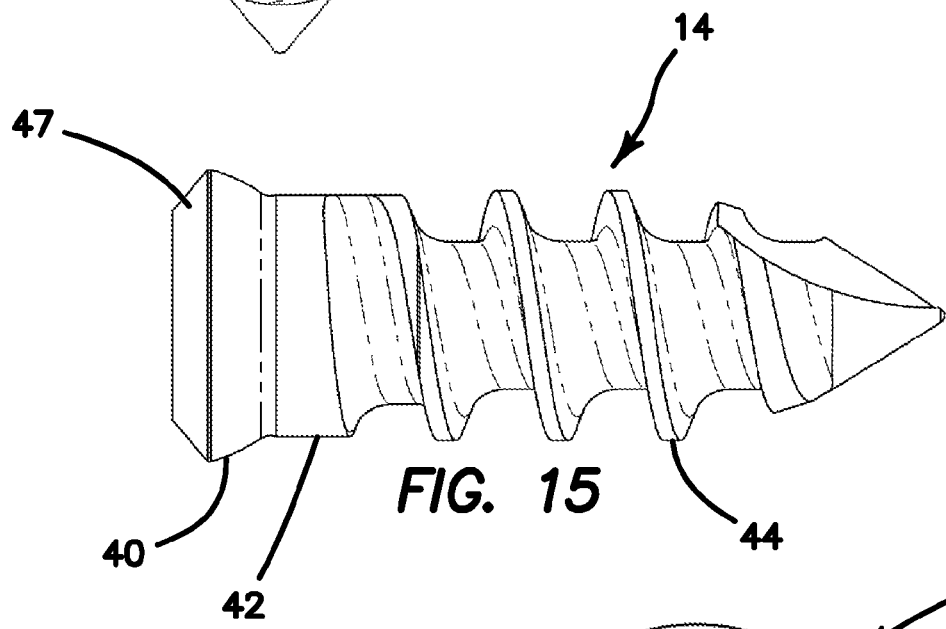
FIG. 15 is a side elevational view of a fastener according to the present invention.
Figure 16:
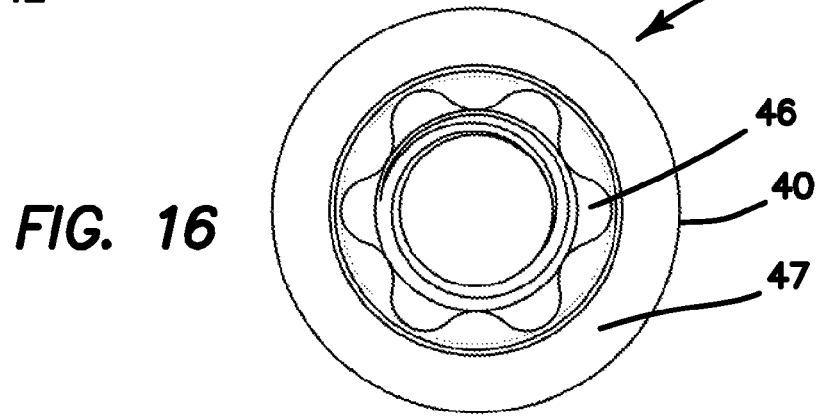
FIG. 16 is a top planar view of a fastener according to the present invention.
Figure 17:
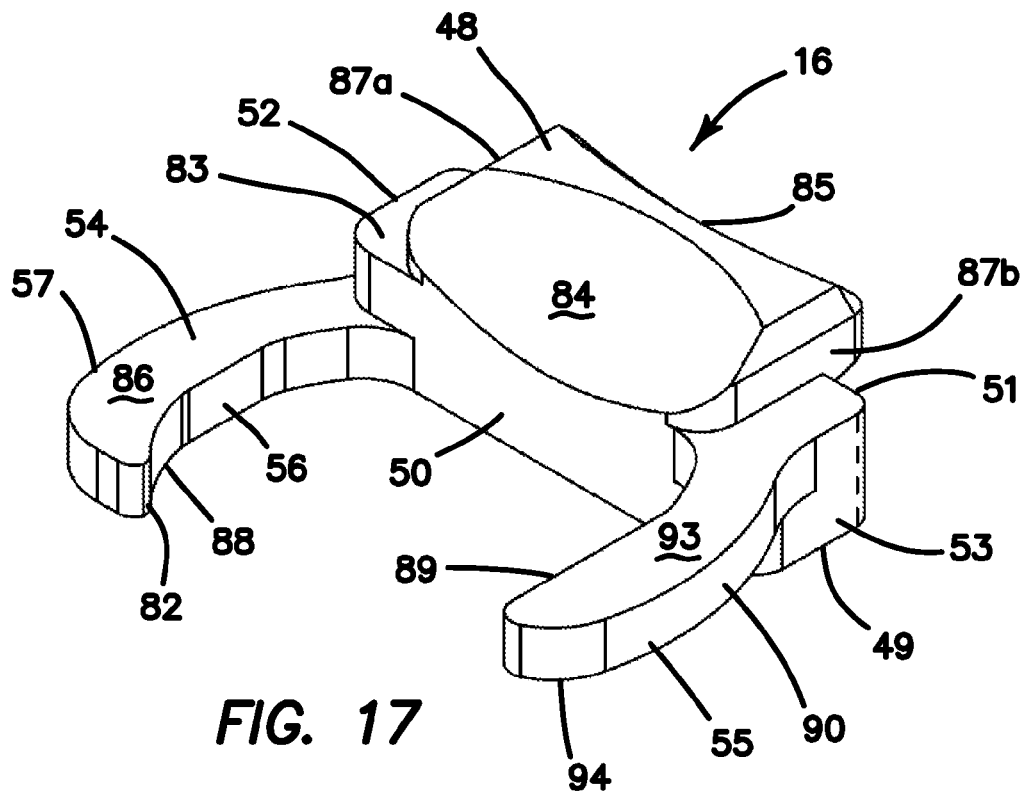
FIG. 17 is a top perspective view of a lock according to the present invention.
Figure 20:
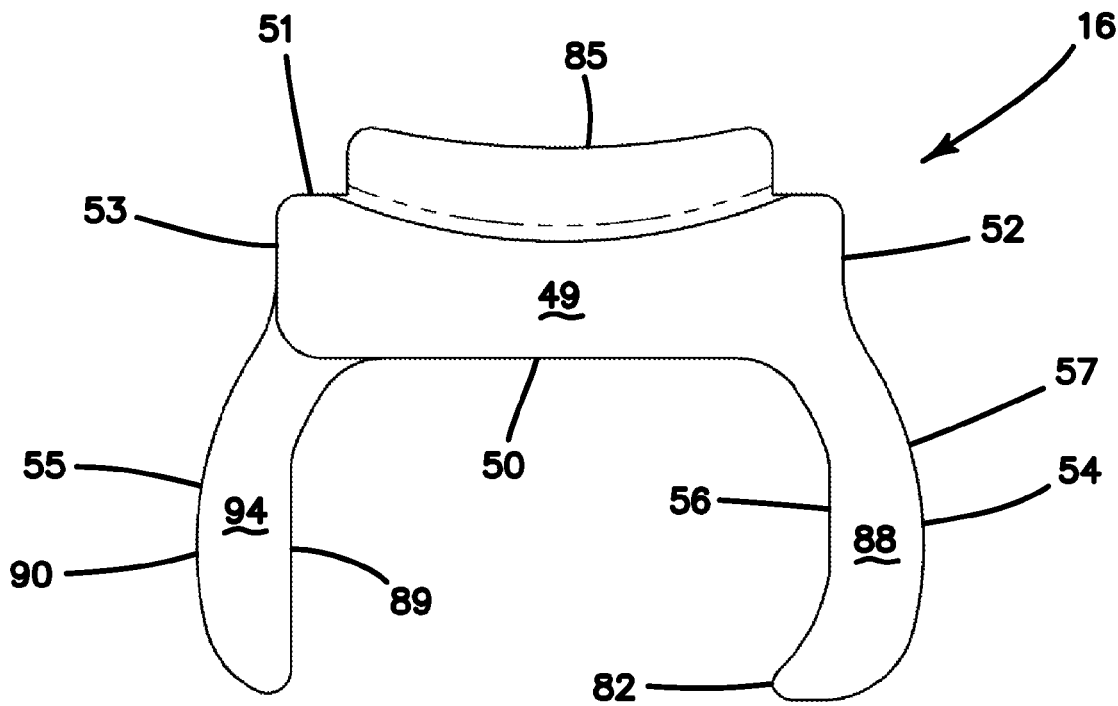
FIG. 20 is a bottom planar view of a lock according to the present invention.
Figure 18:
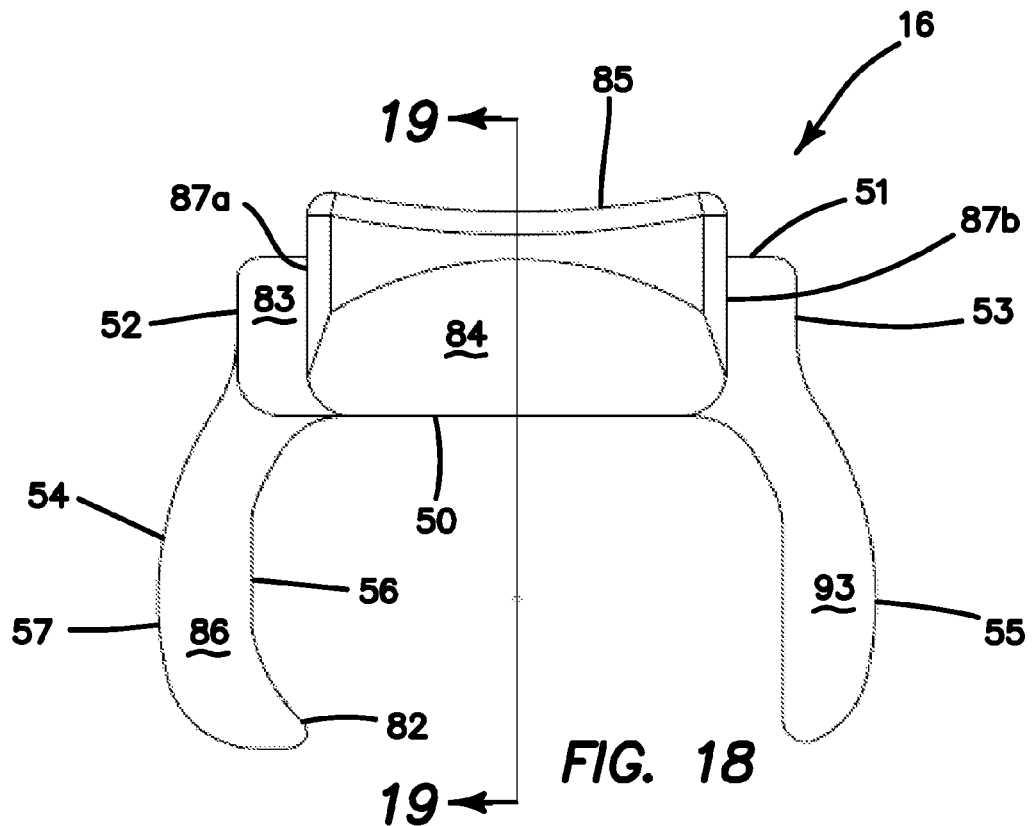
FIG. 18 is a top planar view of a lock according to the present invention.
Figure 19:
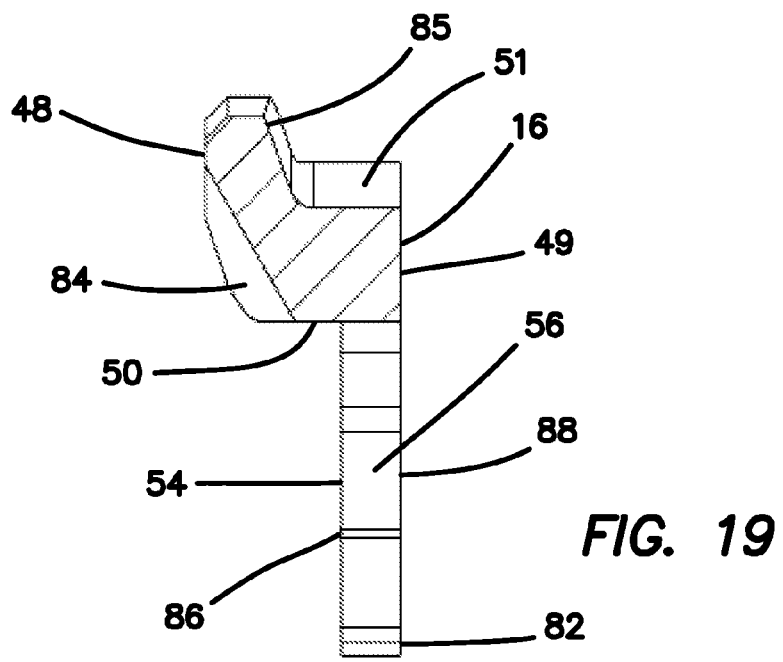
FIG. 19 is a cross-sectional view taken along line 19-19 of FIG. 18 of a lock according to the present invention.
Figure 23:
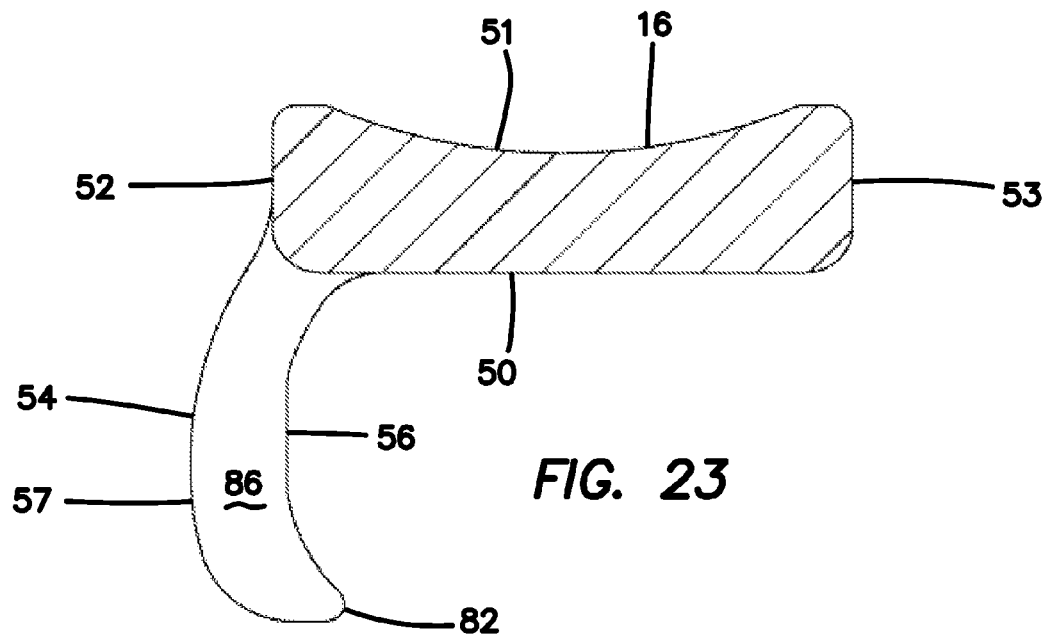
FIG. 23 is a cross-sectional view taken along line 23-23 of FIG. 21 of a lock according to the present invention.
Figure 24:
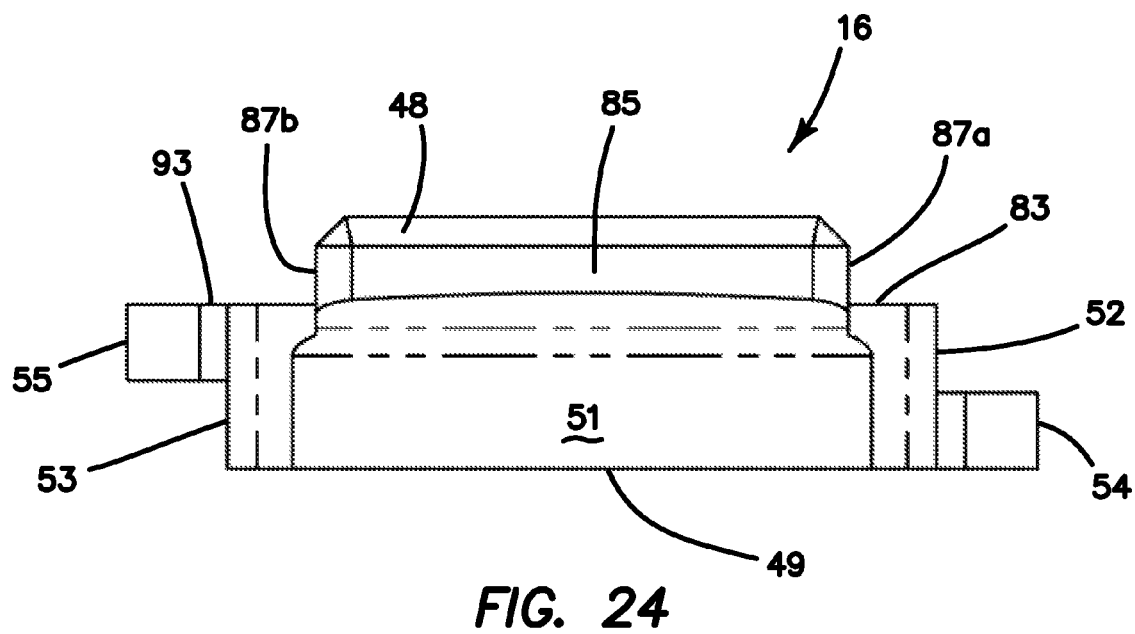
FIG. 24 is an end elevational view of a lock according to the present invention.
Figure 25:
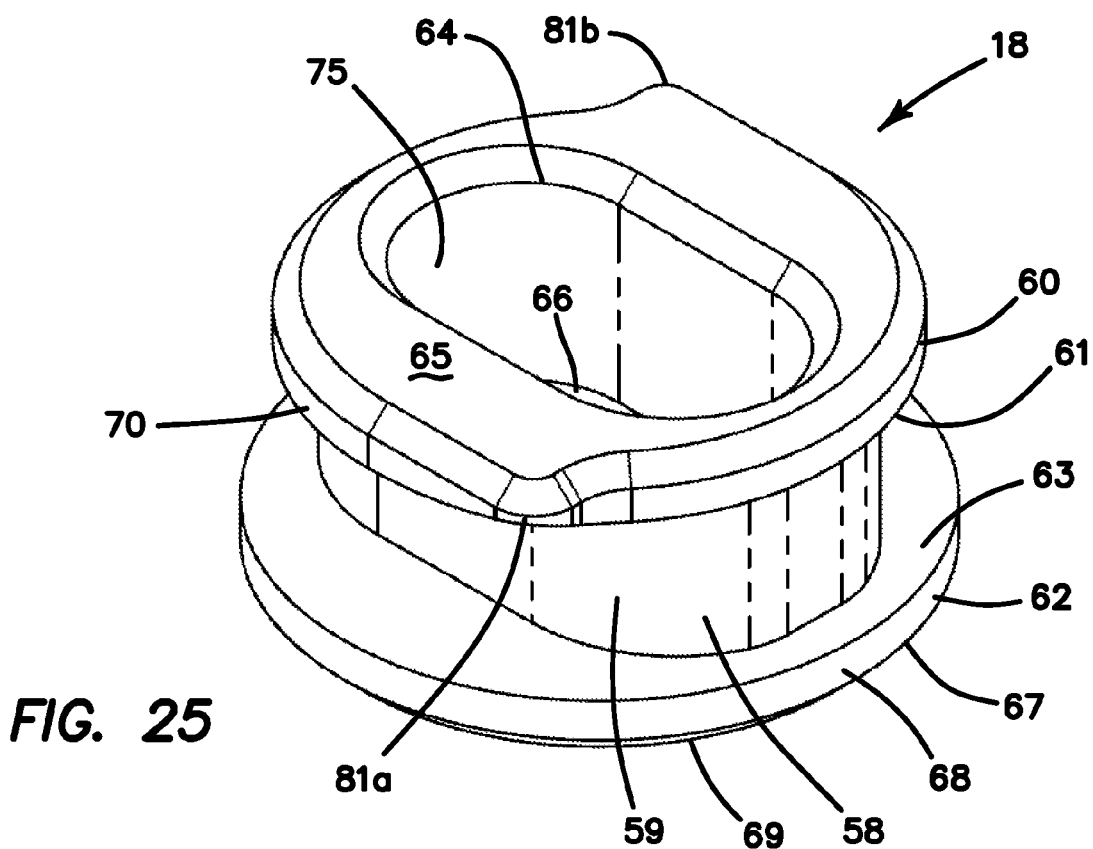
FIG. 25 is a top perspective view of an actuator according to the present invention.

With particular reference to FIGS. 14-16, an exemplary orthopedic fastener 14 that is preferably used with the cervical plate system 10 of the present invention is a bone screw 14. The bone screw 14 includes a screw head 40, neck 42 and threaded shank 44. The head 40 includes a ledge 47 which is a surface along at least a portion of the perimeter of screw head 40. The ledge 47 serves as an abutment surface for a complementary-shaped surface of the lock 16 that acts to cover and retain the fastener 14 to the plate 12. The head 40 includes an instrument recess 46 for receiving a complementary tip of a surgical tool. A substantially hexagonal, daisy-shaped recess 46 is shown in FIGS. 14 and 16, however, the recess 46 can be of any shape that allows a surgical tool to drive the bone screws 14 into the vertebral column. The head 40 of the bone screw 14 corresponds to the shape of the head-receiving portion 26 of the through hole 24 or, in an alternative variation, the inside of an associated retention ring if one is employed. Various bone screws 14 may be employed including ones capable of polyaxial, variable angle or fixed angled orientation with respect to the plate 12 with or without the ability to be locked down at a desired angle or orientation with respect to the plate 12. The bone screws 14 are preferably self-tapping, however, other screws requiring holes to be drilled or pre-tapped can also be employed.

Turning now to FIGS. 17-24, the locks 16 according to the present invention will now be discussed. Each lock 16 includes a top surface 48 and a bottom surface 49 interconnected by an actuator-facing surface 50, a fastener-facing surface 51, a first sidewall 52 and a second sidewall 53. Two finger-like projections 54, 55 extend outwardly from the actuator-facing side or surface 50 of the lock 16. A first finger-like projection 54 has an inner surface 56 that transitions into the actuator-facing surface 50 and an outer surface 57 that transitions into the first sidewall 52. The first sidewall 52 is substantially planar. The outer surface 57 of the first finger projection 54 is curved outwardly relative to the first sidewall 52 and forms a convex shape. The inner surface 56 is slightly curved and forms a substantially concave shape. The inner surface 56 may includes a substantially flat and straight surface between proximal and distal curved ends. At a distal end of the first projection 54, the inner surface 56 and outer surface 57 intersect forming a hook-like feature 82. The hook-like feature 82 is defined by the inner surface 56 or distal end extending toward the other finger-like projection 55. The first finger-like projection 54 includes a top surface 86 and a bottom surface 88 that interconnect with the inner surface 56 and outer surface 57 to define the finger-like projection 54. The bottom surface 88 of the finger-like projection 54 is aligned or substantially even with the bottom surface 49 of the lock 16. The first finger-like projection 54 rises from the bottom surface 49 to approximately half the thickness of the actuator-facing surface 50.

A second finger-like projection 55 has an inner surface 89 that transitions into the actuator-facing surface 50 and an outer surface 90 that transitions into the second sidewall 53. The outer surface 90 of the second finger projection 55 is curved outwardly relative to the second sidewall 53 and forms a convex shape. The inner surface 89 of the second finger-like projection 55 is substantially flat and straight except at the proximal end where the inner surface 89 curves as it transitions into the actuator-facing surface 50. At a distal end of the second finger-like projection 55, the inner surface 89 and outer surface 90 intersect without a hook-like feature. The second finger-like projection 55 includes a top surface 93 and a bottom surface 94 that interconnect with the inner surface 89 and outer surface 90 to define the finger-like projection 55. The bottom surface 94 of the second finger-like projection 55 is at substantially the same height as the top surface 86 of the first finger-like projection 54, that is approximately half-way beneath the top surface 48 of the lock 16. The first finger-like projection 54 has approximately the same height as the second finger-like projection 55. The top surface 48 of the lock 16 includes a scallop 84 near the actuator-facing surface 50. The lock 16 includes a retaining flange 85 that extends outwardly from the fastener-facing surface 51. The retaining flange 85 forms an overhang that is configured to cover and retain the fastener 14 when in the locked orientation. The retaining flange 85 includes a surface that substantially conforms to the ledge on the screw head 47. Two locks 16 are employed for each actuator 18. That is, one actuator 18 is used to simultaneously deploy two locks 16 between an unlocked orientation a locked orientation wherein in the locked orientation the retaining flange 85 of each lock 16 covers/retains the fastener 14 relative to the plate to substantially prevent each fastener 14 from backing out from the through hole 24 of the plate 12. Two identical locks 16 are employed per level per actuator 18. The two locks 16 are oriented with respect to each other such that the staggered finger-like projections 54, 55 are stacked on top of each other. In particular, two locks 16 are oriented such that the actuator-facing surface 50 of each lock 16 are facing each other and the retaining flange 85 of each lock 16 are facing away from each other or toward the fastener 14 or fastener through hole 24. The first finger-like projection 54 of a right first lock 16 is located beneath the second finger-like projection 55 of a left second lock 16 and the second finger-like projection 55 of the right first lock 16 is located above the first finger-like projection 54 of the left second lock 16. Rotation of the actuator 18 pushes both first and second locks 16 outwardly toward the through holes 24 such that the retaining flange 85 of each lock 16 cover and retain respective fasteners 14 relative to the plate 12 in the locked orientation. The locks 16 translate laterally along the lateral axis between the locked position and the unlocked position. The locks 16 are retained with respect to the plate 12 by the surface 83 and surface 93 being located beneath the overhang portion 32 of the plate 12. Surfaces 87a and 87b of the lock 16 are adjacent to transition surface 27b and stop 29a, respectively, and are located there between and permitted to slide there against. The surfaces 87a, 87b of the other lock 16 of the pair are adjacent to transition surface align with and are adjacent to overhang portions The locking and unlocking positions will be described in greater detail below.

Figure 30:
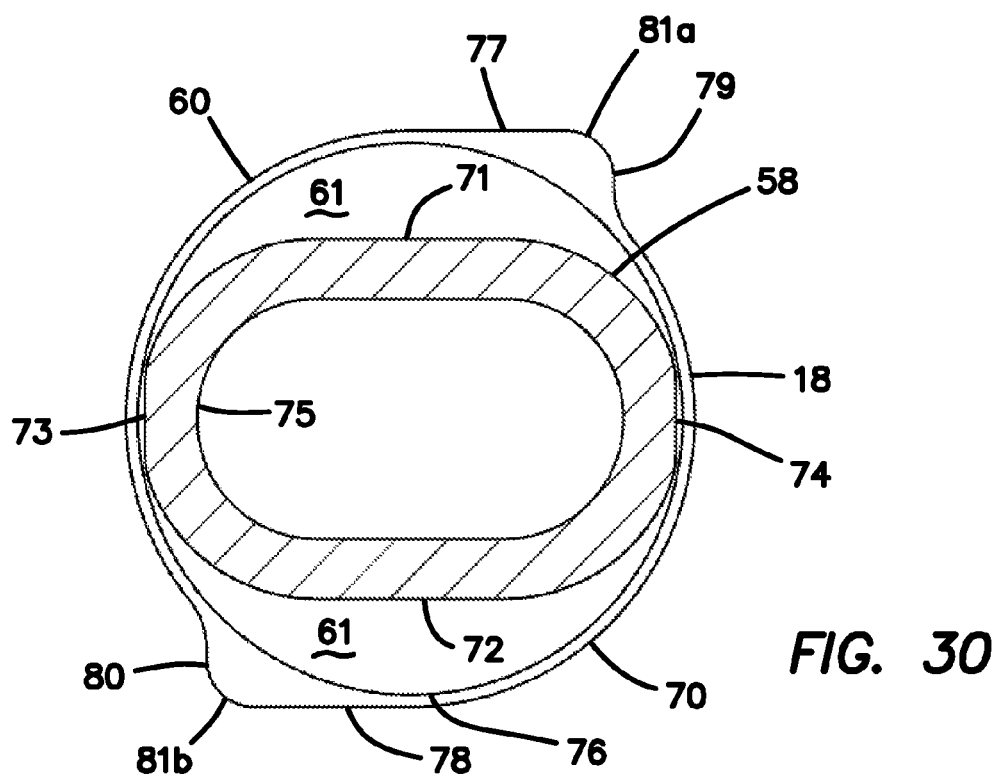
FIG. 30 is a cross-sectional view taken along line 30-30 of FIG. 28 of an actuator according to the present invention.
Figure 28:
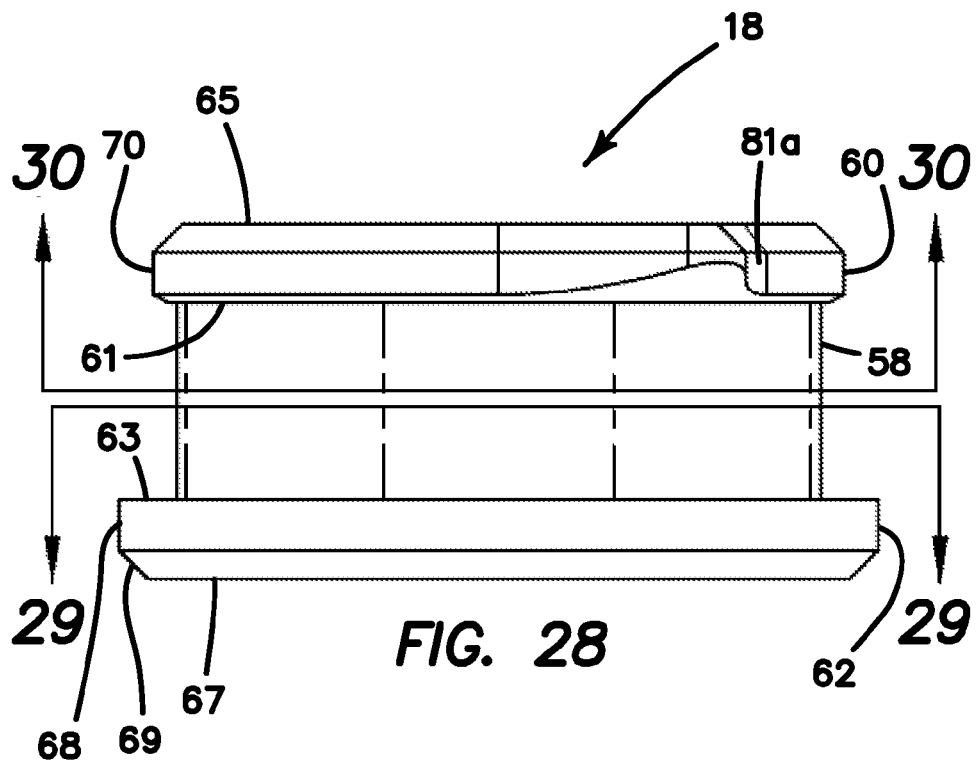
FIG. 28 is a side elevational view of an actuator according to the present invention.
Figure 29:
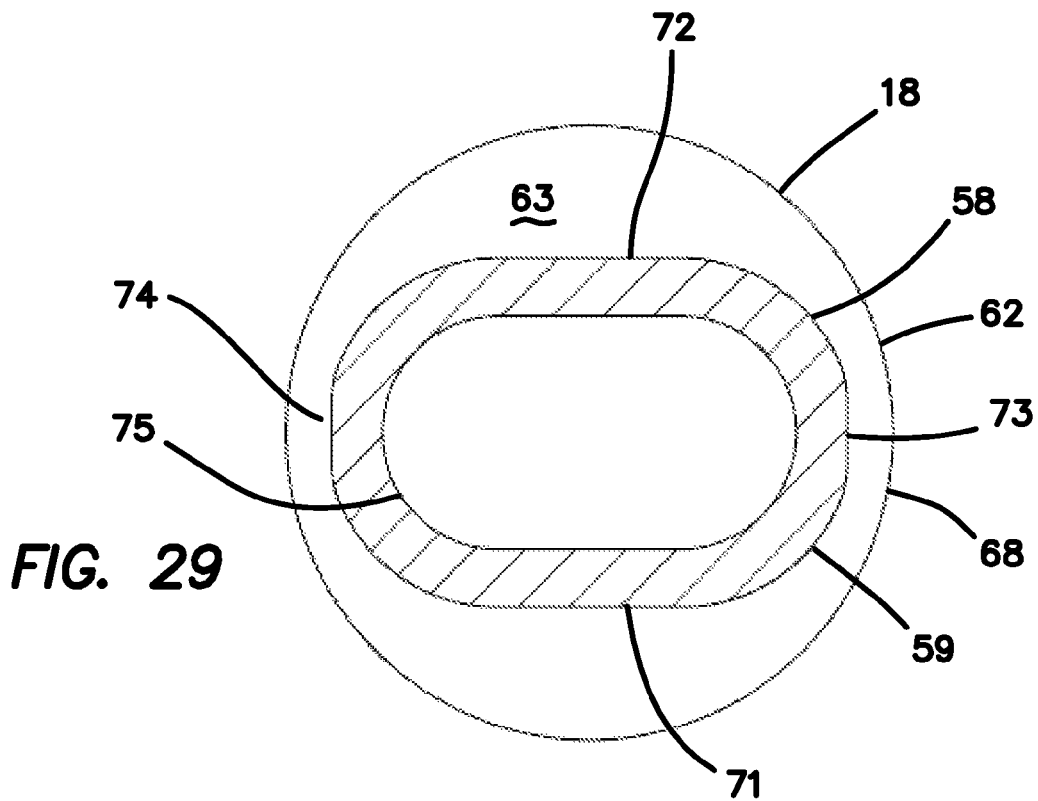
FIG. 29 is a cross-sectional view taken along line 29-29 of FIG. 28 of an actuator according to the present invention.

Turning now to FIGS. 25-30, the actuator 18 will now be discussed. The actuator 18 includes a middle body 58 interconnected between an upper body 60 and a lower body 62. The middle body 58 extends from a bottom surface 61 of the upper body 60 along the longitudinal axis of the actuator 18 to a top surface 63 of the lower body 62. The middle body 58 includes an outer surface 59 and an inner surface 75. The inner surface 75 defines an instrument recess 64 that opens at a top surface 65 of the upper body 60. The instrument recess 64 is configured to receive an instrument to turn the actuator 18 with respect to the plate 12. Although an oval or elliptical instrument recess 64 that is configured to match a complementarily-shaped instrument is shown in FIGS. 25-30, an instrument recess 64 having any shape that is complementary to the instrument employed to activate, move or rotate the actuator 18 is within the scope of the present invention. The instrument recess 64 extends downwardly from the top surface 65 of the upper body 60 to a bottom surface 66 of the recess 64. The middle body 58 has a cross-section taken perpendicular to the longitudinal axis of the actuator 18. In a cross-section of the middle body 58, the outer surface 59 defines a shape having a length greater than a width wherein the length is defined perpendicular to the longitudinal axis of the actuator 18 and the width is defined perpendicular to the length and the longitudinal axis. The outer surface comprises first and second opposing surface portions 71, 72 of the shape generally aligned with the length and third and fourth opposing portions 73, 74 of the shape generally aligned with the width as seen in FIGS. 29 and 30. The outer surface 59 of the middle body 58 can be described as elongate, oval, or rectangular with rounded corners. The first and second opposing surface portions are shown in the variation of FIGS. 25-30 to include substantially flat surface areas. Although the figures illustrate the inner surface 75 having the same shape as the outer surface 59, the invention is not so limited and the inner surface 75 can correspond to the shape of any suitable driver instrument configured rotate the actuator 18.

The lower body 62 of the actuator 18 includes a top surface 63 and a bottom surface 67 interconnected by an outer surface 68. The outer surface 68 includes a circumferential tapered surface 69 that tapers into the bottom surface 67. The lower body 62 is circular in shape and is configured to be inserted into and to be received within the actuator well 36 of the plate 12 and rotate relative to the plate 12. The actuator 18 may be configured snap into the plate 18 well 36 such that the actuator is connected yet free to rotate.

The upper body 60 of the actuator 18 includes a top surface 65 interconnected to a bottom surface 61 by an outer surface 70. The upper body 60 is a disc substantially defining a circle 76. In a cross-section of the upper body 60 taken perpendicular to the longitudinal axis of the actuator 18, the upper body 60 includes two diametrically opposite tangential lines 77, 78 that are substantially parallel to each other as best seen in FIG. 30. These tangential lines 77, 78 transition smoothly into abutment lines 79, 80, respectively. These abutment lines 79, 80 form abutment surfaces in the upper body 60 that are configured to rotate into contact with stops 29a, 29b, respectively, in the unlocked orientation. Together the tangential lines 77, 78 and abutment lines 79, 80 define two diametrically opposed protrusions 81a, 81b that extend outwardly. One skilled in the art will understand that these protrusions 81a, 81b need not necessarily be formed by the tangential lines 77, 78 and abutment lines 79, 80 and any suitable protrusion is within the scope of the present invention.

Figure 31:
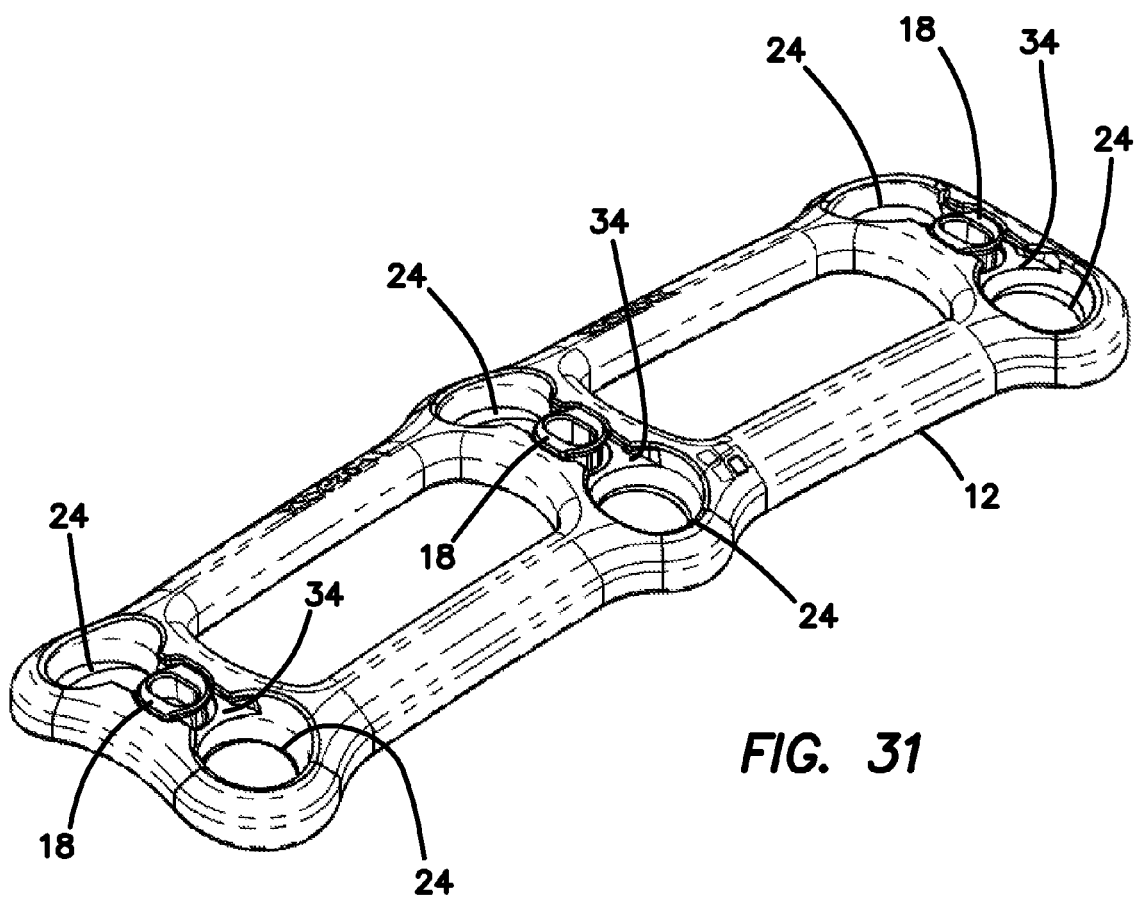
FIG. 31 is a top perspective view of a plate with actuators in locked configurations according to the present invention.

Turning to FIG. 31, the cervical plate system 10 is assembled by first inserting the actuators 18 into the recesses 34 such that the length of the middle body 58 of the actuator is substantially parallel to the lateral axis of the plate 12 which is the locked orientation of the actuator 18. The lower body 62 is disposed inside the actuator well 36 of the plate 12. Next, with reference to FIGS. 32-34, the locks 16 are inserted into the recesses 34. A first lock 16 with its finger-like projections 54, 55 facing the actuator 18 is inserted on the right side of the actuator 18 and a second lock 16 with its finger-like projections 54, 55 facing the actuator 18 is inserted on the left side of the actuator 18. Because of the configuration of the locks 18, the finger-like projections are stacked or otherwise located above each other and adjacent to the first and second opposing surfaces 71, 72 of the actuator 18 along the length of the shape of the middle body 58. The third and fourth opposing surfaces 73, 74 are oriented adjacent to the actuator-facing surfaces 50 of the locks 16. The fingers 54, 55 snap into place as their outer surfaces 57, 90 slide past protrusions 23a, 23b, 25a, 25b. The overhang portion 32 of the plate 12 retains the locks 16 from falling out of the plate along the z-axis and the locks prevent the actuator from falling out of the plate as the locks 16 contact the top surface 63 of the lower body 62 of the actuator 18 to prevent them from z-axis translation wherein the z-axis in the figures is perpendicular to the face of the page. As can be seen in FIG. 34, the retaining flange 85 of the locks 16 protrude into and above the through holes 24 for fastener 14 retention.

Figure 32:
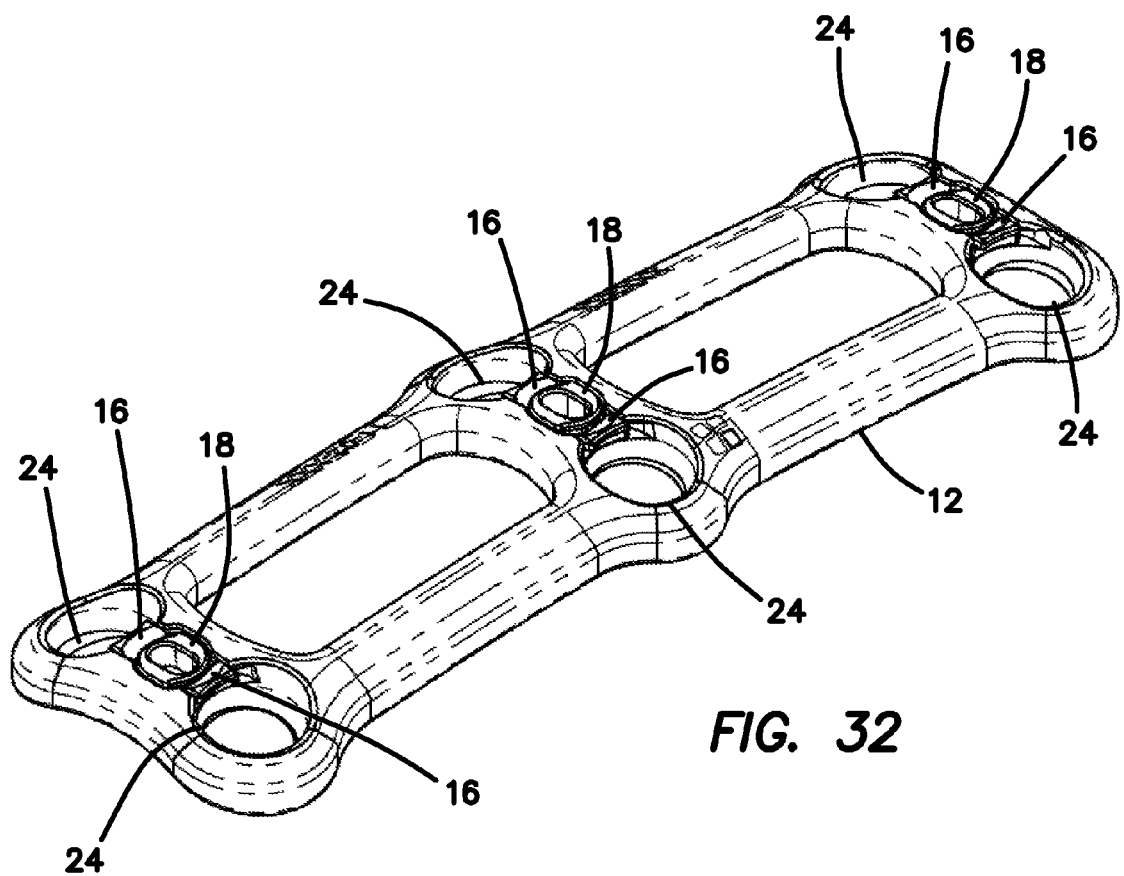
FIG. 32 is a top perspective view of a plate with actuators and locks in locked configurations according to the present invention.
Figure 33:
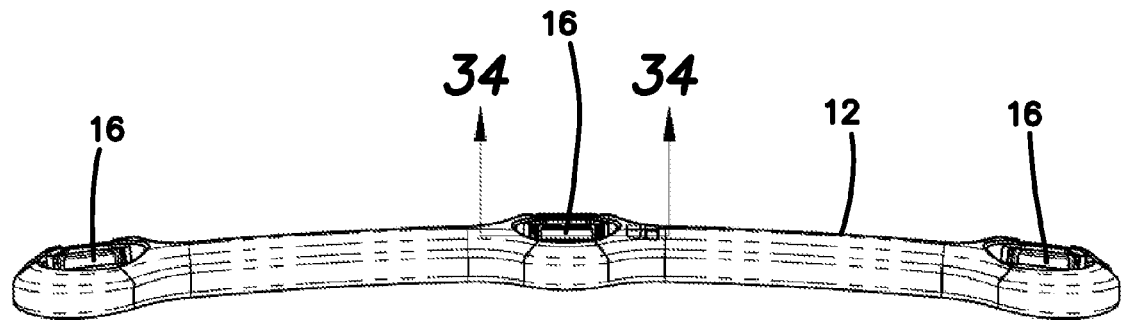
FIG. 33 is a side elevational view of a plate with actuators and locks in locked configurations according to the present invention.
Figure 34:
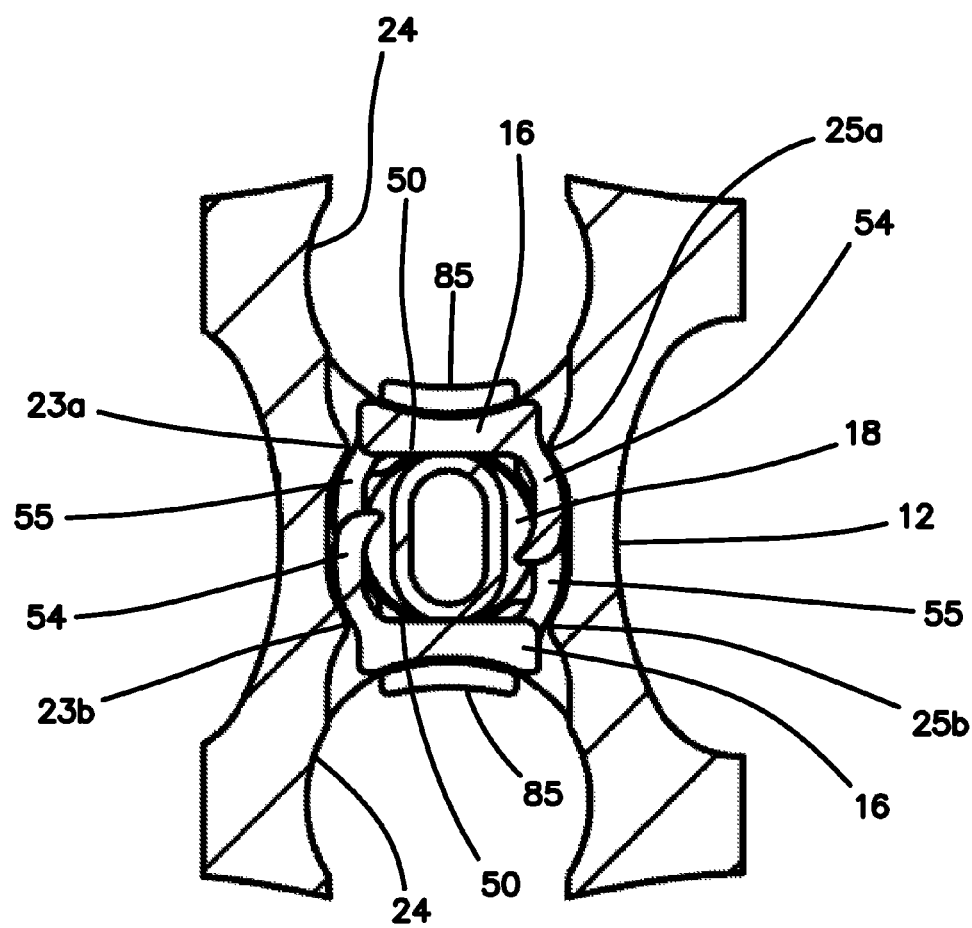
FIG. 34 is a cross-sectional view taken along line 34-34 of FIG. 33 of a plate with an actuator and locks in a locked configuration according to the present invention.
Figure 35:
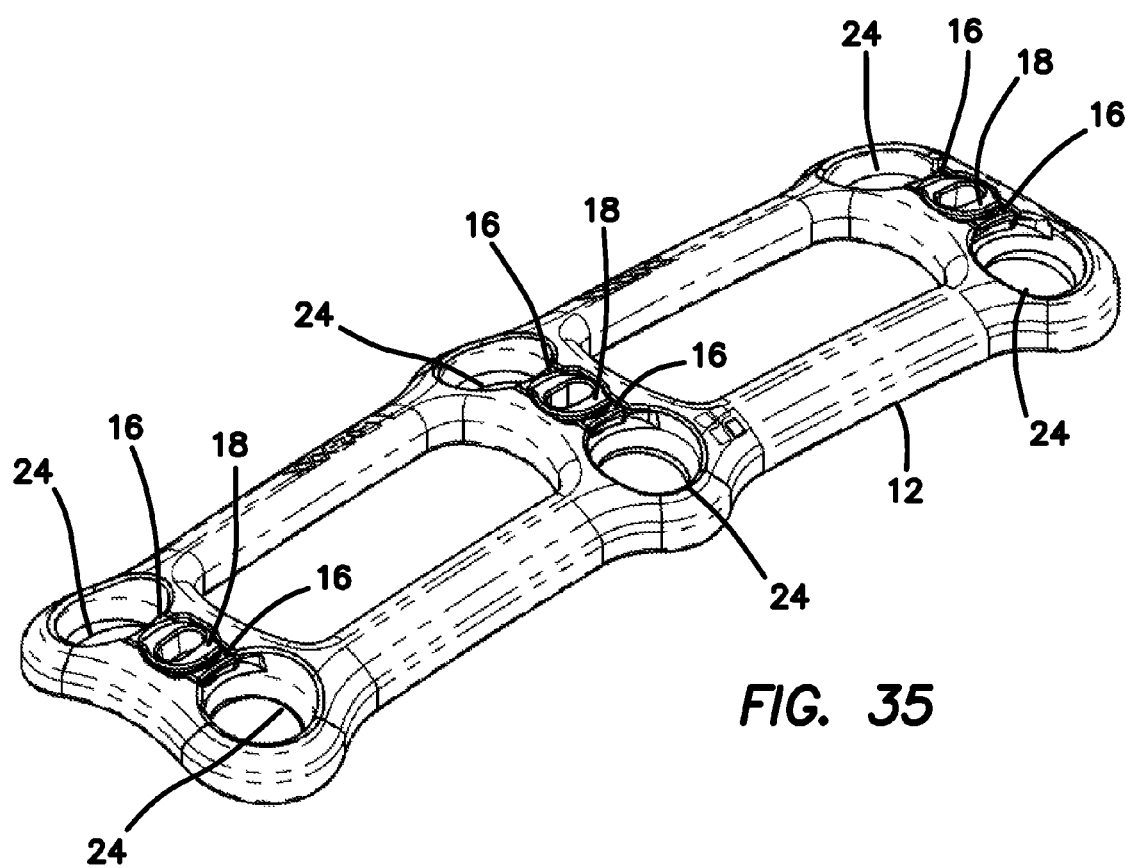
FIG. 35 is a top perspective view of a plate with actuators and locks in unlocked configurations according to the present invention.
Figure 36:
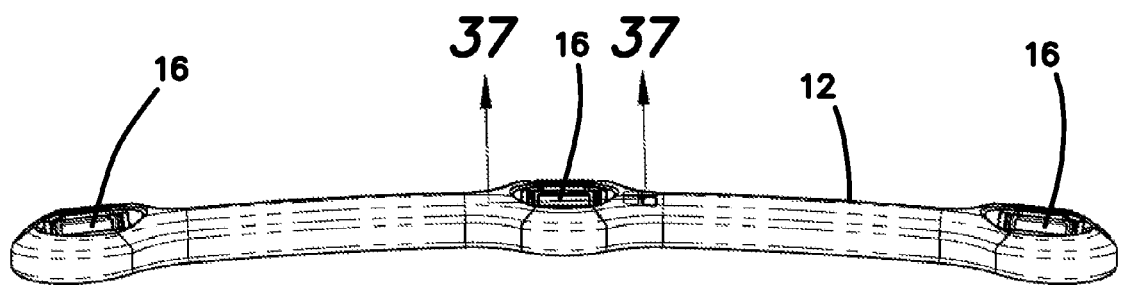
FIG. 36 is a side elevational view of a plate with actuators and locks in unlocked configurations according to the present invention.
Figure 37:
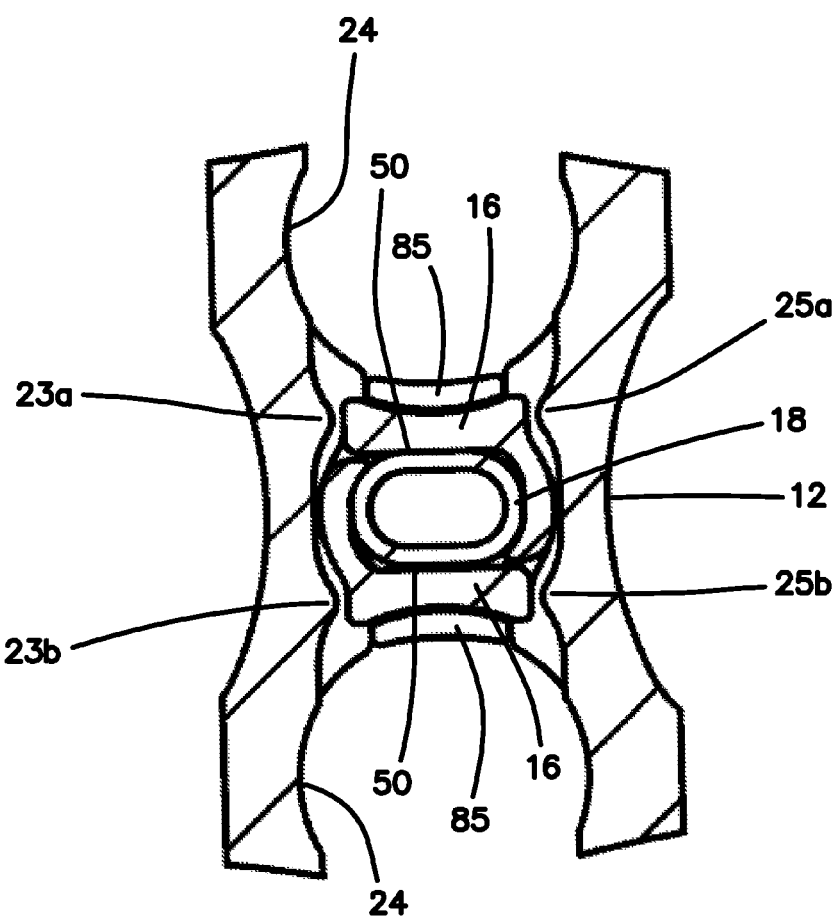
FIG. 37 is a cross-sectional view taken along line 37-37 of FIG. 36 of a plate with an actuator and locks in an unlocked configuration according to the present invention.

With reference to FIGS. 35-37, the final step of assembly includes rotating the actuator 18 from the locked orientation shown in FIGS. 32-34 to the unlocked orientation shown in FIGS. 35-37. With particular reference to FIG. 34, the actuator 18 will be rotated clockwise in the view of FIG. 34 into the unlocked orientation. As the actuator 18 is rotated the middle body 58 will catch the hook-like features 82 on the first finger-like projections 54, thereby pulling the locks 16 closer together and out of interference with the through holes 24. The pulled-in or locked orientation of the locks 16 is shown in FIG. 37 in which the length of the shape of the middle body 58 is substantially aligned with the longitudinal axis of the plate 12 and the finger-like projections 54, 55 substantially located between protrusions 23a, 23b, 25a, 25b. With the actuator 18 and locks 16 in an unlocked orientation, fasteners 14 may be inserted into the through holes 24 of the plate 12.

Figure 38:
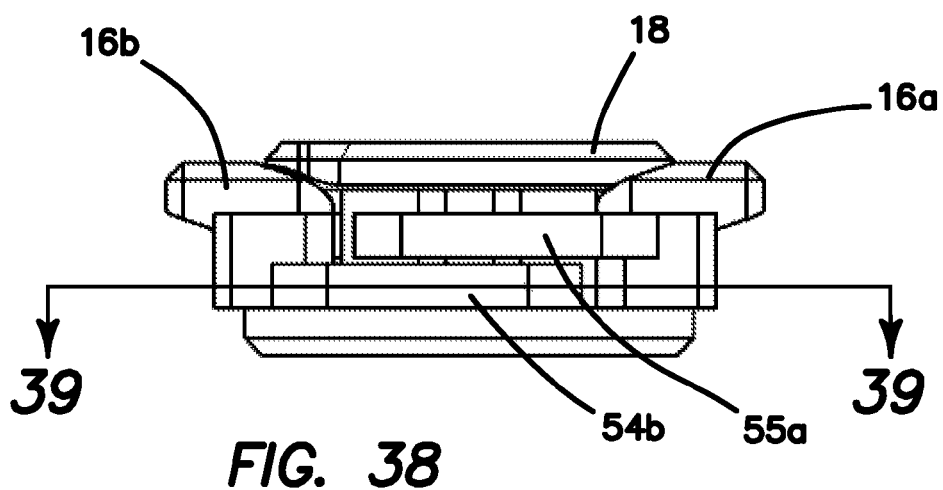
FIG. 38 is a side elevational view of an actuator and two locks in an unlocked configuration according to the present invention.
Figure 39:
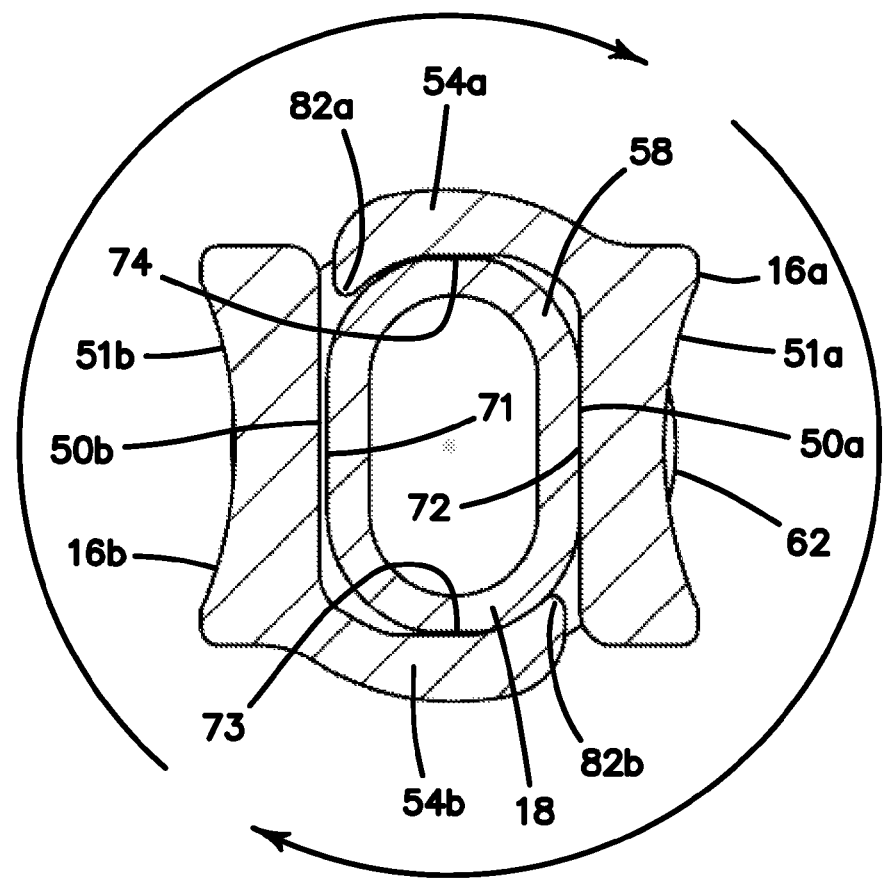
FIG. 39 is a cross-sectional view taken along line 39-39 of FIG. 38 of an actuator and two locks according to the present invention.
Figure 40:
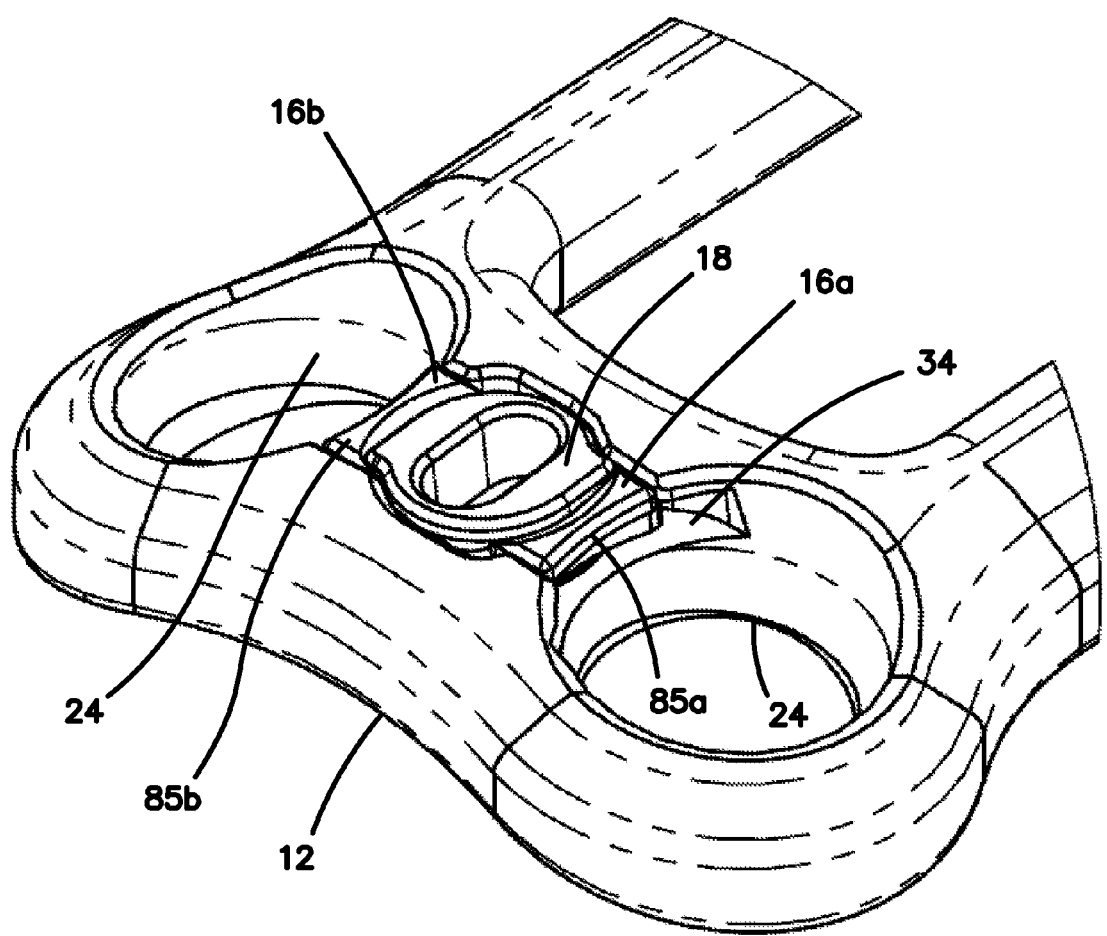
FIG. 40 is a top perspective sectional view of a plate in an unlocked configuration according to the present invention.

Turning now to FIG. 38, there is shown an actuator 18 and two locks 16a and 16b in an unlocked orientation without the plate 12. FIG. 38 shows finger 55a of lock 16a located above finger 54b of lock 16b. FIG. 39 also illustrates the actuator 18 and locks 16a, 16b in an unlocked orientation in which finger 54a is adjacent to fourth opposing surface 74, finger 54b adjacent to the third opposing surface 73, the actuator-facing surface 50b adjacent to the first opposing surface 71, and the actuator-facing surface 50a adjacent to the second opposing surface 72. The arrows in FIG. 39 indicate the clockwise direction in which the actuator 18 is to be rotated to achieve the locked configuration from the unlocked configuration. As rotation of the actuator 18 is commenced in the clockwise direction, the intersection of second and fourth opposing surfaces 72, 74 will cam against the actuator-facing surface 50a and simultaneously the intersection of first and third opposing surfaces 71, 73 will cam against the actuator-facing surface 50b and because of the elongate middle body 58 of the actuator 18, the locks 16a, 16b will be spread apart as rotation continues and the length of the shape of the middle body 58 is aligned with the lateral axis of the plate 12. FIG. 29 shows the length of the shape of the middle body 58 being aligned with the longitudinal axis of the plate 12. FIG. 40 illustrates the locks 16a, 16b inside the recess 34 with the retaining flanges 85a, 85b retracted and clear out of the way of the through holes 24 when in the unlocked configuration. Fasteners 14 may be inserted and removed when in the unlocked configuration.

Figure 41:
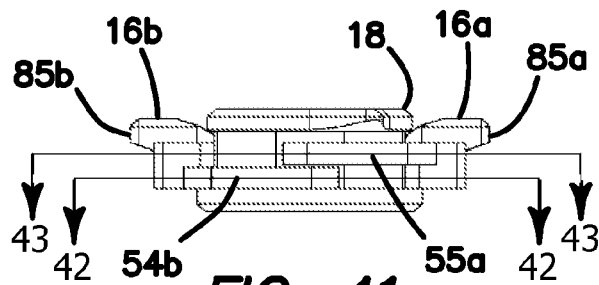
FIG. 41 is a side elevational view of an actuator and two locks in a locked configuration according to the present invention.
Figure 42:
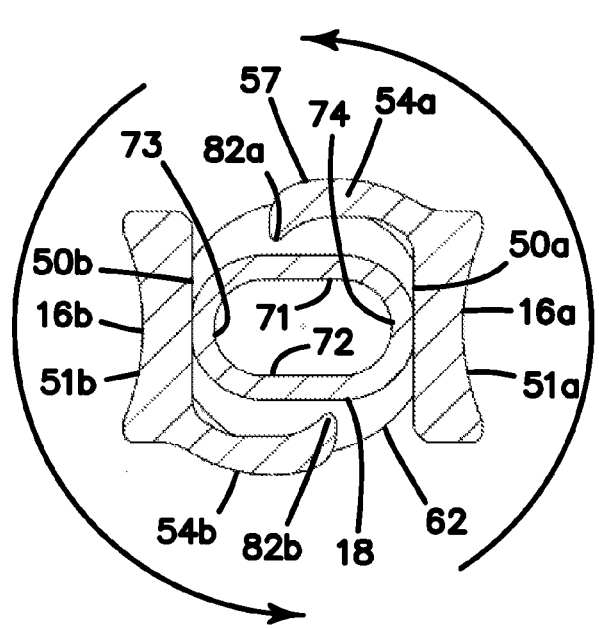
FIG. 42 is a cross-sectional view taken along line 42-42 of FIG. 41 of an actuator and two locks in a locked configuration according to the present invention.
Figure 43:
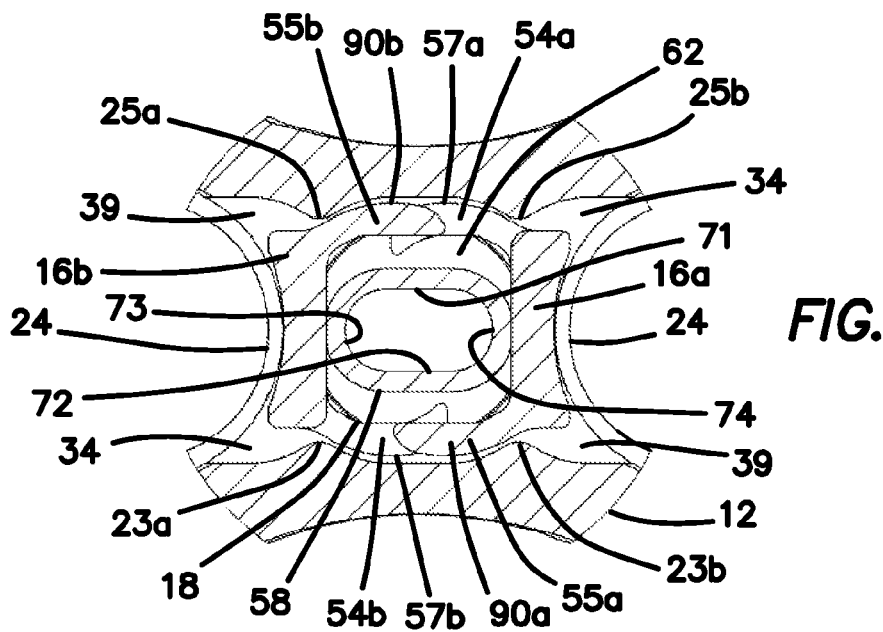
FIG. 43 is a cross-sectional view taken along line 43-43 of FIG. 41 of an actuator and two locks in a locked configuration according to the present invention.
Figure 44:
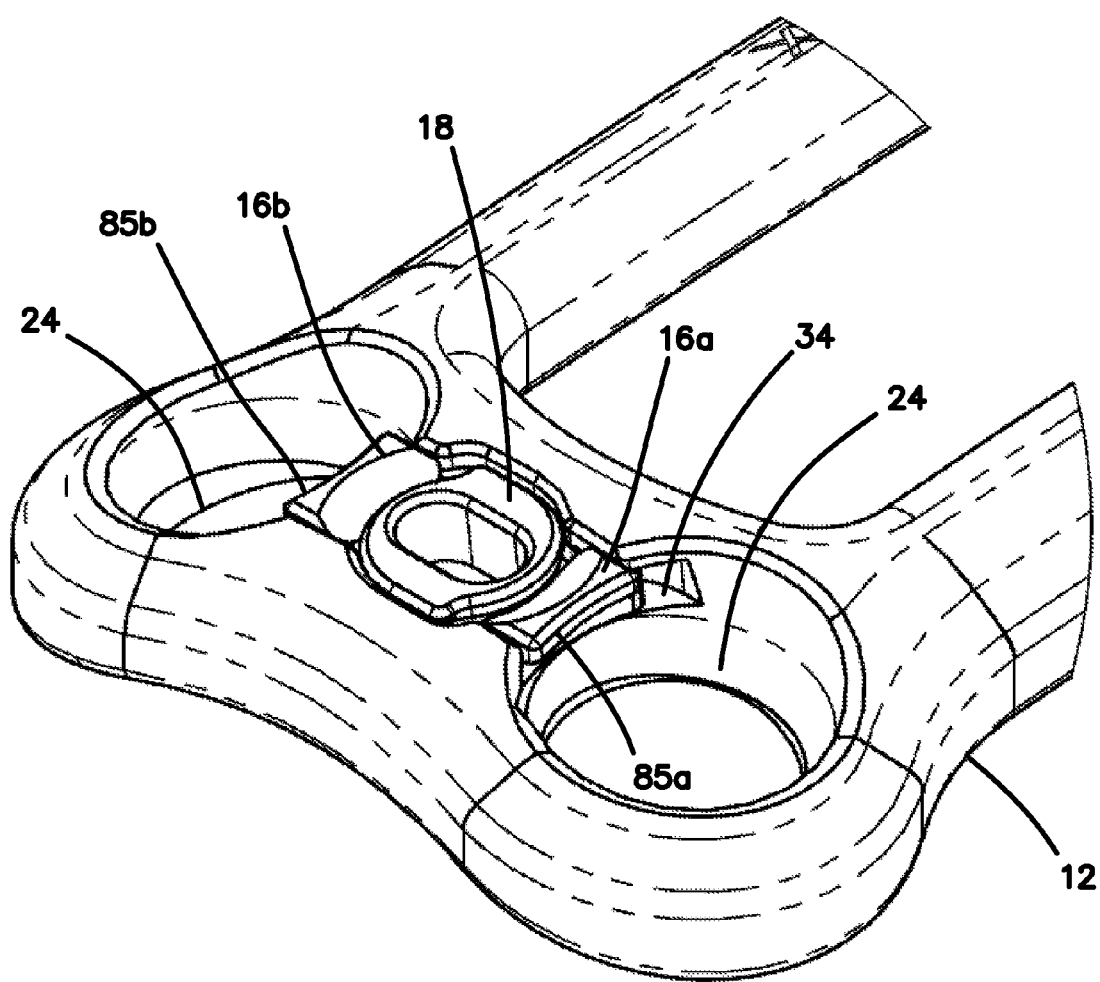
FIG. 44 is a top perspective sectional view of a plate in a locked configuration according to the present invention.

Turning now to FIG. 41, there is shown an actuator 18 and two locks 16a and 16b in a locked orientation without the plate 12. FIG. 41 shows the locks 16a, 16b extended away from the actuator 18 with the retaining flanges 85a, 85b in their most distally extended position for covering and retaining fasteners 14. FIG. 42 illustrates the actuator 18 rotated into a locked position and locks 16a, 16b pushed apart in a locked orientation in which finger 54a is adjacent to the first opposing surface 71, finger 54b adjacent to the second opposing surface 72, the actuator-facing surface 50b adjacent to the third opposing surface 73, and the actuator-facing surface 50a adjacent to the fourth opposing surface 74. The arrows in FIG. 42 indicate the counterclockwise direction in which the actuator 18 is to be rotated to achieve the unlocked configuration from the locked configuration shown. As rotation of the actuator 18 is commenced in the counterclockwise direction, the intersection of first and fourth opposing surfaces 71, 74 will contact the hook 82a and simultaneously the intersection of second and third opposing surfaces 72, 73 will contact the hook 82b and because of the elongate middle body 58 of the actuator 18, such contact with the hooks and rotation of the body through approximately 90 degrees will result in the locks 16a, 16b being drawn inwardly and pulled closer to the actuator 18 into the unlocked configuration as shown in FIG. 39. The length of the shape of the middle body 58 is aligned with the lateral axis of the plate 12 in the locked configuration. The cross-sectional view of FIG. 42 shows all position of all four fingers 54a, 54b, 55a, 55b in the locked configuration and with respect to the plate 12. The convex outer surfaces 57a, 90b are located between the protrusions 25a, 25b in the plate 12 and the convex outer surfaces 57b, 90a are located between the protrusions 23a and 23b in the plate 12 when in the locked configuration. FIG. 44 illustrates the locks 16a, 16b positioned inside the recess 34 with the retaining flanges 85a, 85b protruding into the pathway of the through holes 24 so as to retain fasteners 14 located therein. The fasteners 14 are prevented from backing out with respect to the plate 12 when in the locked configuration.

Although this application discloses certain embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above.

We claim:

1. A bone plate system, comprising:
a plate having two adjacent through holes; each through hole configured to receive a bone fastener for attaching the plate to bone;
an actuator located between the two through holes; the actuator having a longitudinal axis and an outer surface; in cross-section of the actuator taken perpendicular to the longitudinal axis of the actuator, the outer surface defines a shape having a length greater than a width wherein the length is defined perpendicular to the longitudinal axis of the actuator and the width is defined perpendicular to the length and the longitudinal axis; the outer surface comprising first and second opposing surface portions of the shape generally aligned with the length and third and fourth opposing surface portions of the shape generally aligned with the width; the actuator being connected to the plate such that the actuator rotates with respect to the plate;
two locks movably coupled to the plate; each lock having a pair of fingers oppositely disposed from a fastener retaining flange; the fastener retaining flange of one lock being located between the actuator and one of the through holes; the fastener retaining flange of the other lock being located between the actuator and the other one of the through holes; the actuator being located between the fingers of both locks;
two bone fasteners; each bone fastener having a head portion and configured for insertion into a through hole such that at least a portion of the head portion is positioned distally of the fastener retaining flange; and
wherein bone plate includes an unlocked configuration in which the fastener retaining flanges are out of the pathway of the through holes to permit passage of the bone fasteners into or out of the through holes;
wherein the bone plate includes a locked configuration in which the fastener retaining flanges are in the pathway of the through holes and above at least a portion of the fasteners to prevent the bone fasteners from backing out of the through holes; and
wherein the actuator is movable between a locked and unlocked configuration by rotation of the actuator relative to the plate which simultaneously moves both locks between the locked and unlocked configurations.

2. The bone plate system of claim 1 wherein the length of the shape of the actuator cross-section is substantially perpendicular to a lateral axis of the plate in the unlocked configuration.

3. The bone plate system of claim 1 wherein the length of the shape of the actuator cross-section is substantially parallel to a lateral axis of the plate in a locked configuration.

4. The bone plate of claim 1 wherein the plate includes a recess located between the two through holes; the actuator and two locks being located in the recess.

5. The bone plate system of claim 4 wherein the recess includes two oppositely disposed sidewalls; the sidewalls extend upwardly from a base surface of the recess to a top surface of the plate; the sidewalls have protrusions extending inwardly toward the recess; the protrusions being configured to limit translation of the locks along the lateral axis.

6. The bone plate system of claim 5 wherein the fingers include an outer surface having a convex shape configured to be retained between the protrusions.

7. The bone plate system of claim 4 wherein the recess includes two oppositely disposed sidewalls; the sidewalls extend upwardly from a base surface of the recess to a top surface of the plate; each sidewall having an overhanging portion near the top surface of the plate; the overhanging portion extends inwardly toward the recess; the overhanging portion is configured to retain the locks and actuator inside the recess.

8. The bone plate system of claim 7 wherein the overhanging portion along at least one of the sidewalls includes a stop configured to abut a surface on the actuator and limit rotation of the actuator.

9. A bone plate system, comprising:
a plate having two adjacent through holes; each through hole configured to receive a bone fastener for attaching the plate to bone;
an actuator located between the two through holes; the actuator having a longitudinal axis and an outer surface; in cross-section of the actuator taken perpendicular to the longitudinal axis of the actuator, the outer surface defines a shape having a length greater than a width wherein the length is defined perpendicular to the longitudinal axis of the actuator and the width is defined perpendicular to the length and the longitudinal axis; the outer surface comprising first and second opposing surface portions of the shape generally aligned with the length and third and fourth opposing surface portions of the shape generally aligned with the width; the actuator being connected to the plate such that the actuator rotates with respect to the plate;
two locks movably coupled to the plate; each lock having a pair of fingers oppositely disposed from a fastener retaining flange; the fastener retaining flange of one lock being located between the actuator and one of the through holes; the fastener retaining flange of the other lock being located between the actuator and the other one of the through holes; the actuator being located between the fingers of both locks;
two bone fasteners; each bone fastener having a head portion and configured for insertion into a through hole such that at least a portion of the head portion is positioned distally of the fastener retaining flange; and
wherein the bone plate includes an unlocked configuration in which the fastener retaining flanges are out of the pathway of the through holes to permit passage of the bone fasteners into or out of the through holes;
wherein the bone plate includes a locked configuration in which the fastener retaining flanges are in the pathway of the through holes and above at least a portion of the fasteners to prevent the bone fasteners from backing out of the through holes; and wherein the actuator is movable between a locked and unlocked configuration by rotation of the actuator relative to the plate which simultaneously moves both locks between the locked and unlocked configurations wherein each lock includes at least one finger with a hook-like feature configured to contact the actuator to pull the locks inwardly toward the actuator when moving from the locked configuration to the unlocked configuration.

10. A bone plate system, comprising:
- a plate having two adjacent through holes; each through hole being configured to receive a bone fastener for attaching the plate to bone;
- an actuator located between the two through holes; the actuator being connected to the plate such that the actuator rotates with respect to the plate;
- a first lock comprising a first finger and a second finger extending outwardly from an actuator-facing surface; a fastener retaining flange extending outwardly from a fastener-facing surface; the first and second fingers being spaced apart and configured to receive the actuator between the first and second fingers;
- a second lock comprising a third finger and a fourth finger extending outwardly from an actuator-facing surface; a fastener retaining flange extending outwardly from a fastener-facing surface; the third and fourth fingers being spaced apart and configured to receive the actuator between the third and fourth fingers;
- wherein the first finger is located beneath the fourth finger; the second finger is located above the third finger; and the actuator is located between the first, second, third and fourth fingers;
- wherein the bone plate system includes an unlocked configuration and a locked configuration configured such that as the actuator is rotated from the unlocked configuration to a locked configuration, the actuator pushes both locks simultaneously outwardly away from the actuator; and as the actuator is rotated from the locked configuration to the unlocked configuration the actuator simultaneously moves both locks inwardly toward the actuator.

11. The bone plate system of claim 10 wherein the actuator includes an elongated body and rotation of the elongated body pushes both locks simultaneously outwardly.

12. The bone plate system of claim 10 wherein the actuator includes an elongated body and at least one of the first and second fingers includes a hook-like feature at the distal end of the finger and at least one of the third and fourth fingers includes a hook-like feature at the distal end of the finger; wherein as the actuator is rotated from the locked configuration to the unlocked configuration, the elongated body catches the hook-like features on the fingers to pull the locks inwardly towards the actuator.

13. The bone plate system of claim 10 wherein the fastener retaining flange of first lock is located between the actuator and one of the through holes and the fastener retaining flange of the second lock is located between the actuator and the other one of the adjacent through holes.

14. The bone plate system of claim 10 further including at least two bone fasteners; each bone fastener having a head portion and configured for insertion into a through hole such that at least a portion of the head portion is positioned distally of the fastener retaining flange.

15. The bone plate system of claim 14 wherein the fastener retaining flanges of the first and second locks are out of the pathway of the through holes to permit passage of bone fasteners into or out of the through holes when in the unlocked configuration; and the fastener retaining flanges are in the pathway of the through holes configured to prevent bone fasteners from translating proximally of the retaining flanges.

16. The bone plate system of claim 10 wherein the actuator has a longitudinal axis and an outer surface; in cross-section of the actuator taken perpendicular to the longitudinal axis, the outer surface defines a shape having a length greater than a width wherein the length is defined perpendicular to the longitudinal axis of the actuator and the width is defined perpendicular to the length and the longitudinal axis; the outer surface comprising first and second opposing surface portions of the shape generally aligned with the length and third and fourth opposing surface portions of the shape generally aligned with the width.

17. A bone plate system, comprising:
- a plate having two through holes adapted to receive fasteners;
- an actuator comprising an elongated body; and
- two locks; each lock including a pair of fingers oppositely disposed from a fastener retaining flange; one of the pair of fingers including a hook at the distal end of the finger;
- wherein the actuator and two locks are connected to the plate such that the actuator and two locks are movable with respect to the plate; the actuator and two locks being located between the two through holes such that the retaining flanges face the through holes and the fingers face each other; the actuator is located between the fingers;
- wherein the bone plate system includes a locked position and unlocked position;
- wherein as the actuator is rotated from an unlocked to a locked position, the elongated body pushes both locks simultaneously outwardly to retain fasteners placed inside the through holes; and as the actuator is rotated in an opposite direction to an unlocked position, the elongated body catches the hooks on the locks to pull the locks inwardly away from the through holes.

18. The bone plate system of claim 17 wherein the actuator has a longitudinal axis and an outer surface; the elongated body being defined in cross-section of the actuator taken perpendicular to the longitudinal axis, wherein the outer surface defines a shape having a length greater than a width wherein the length is defined perpendicular to the longitudinal axis of the actuator and the width is defined perpendicular to the length and the longitudinal axis; the outer surface comprising first and second opposing surface portions of the shape generally aligned with the length and third and fourth opposing surface portions of the shape generally aligned with the width.

19. The bone plate system of claim 17 wherein the fingers of each pair of fingers of a lock are spaced apart from each other.

20. The bone plate system of claim 17 wherein a finger of the first lock is located above a finger of the second lock along one side of the actuator and a finger of the second lock is located above a finger of the first lock along the opposite side of the actuator.

* * * * *